(12) United States Patent
Dowd et al.

(10) Patent No.: US 12,178,424 B2
(45) Date of Patent: Dec. 31, 2024

(54) SUTURING BREAKAWAY ANCHOR STRIP

(71) Applicant: Aurora Medical Technologies Corp, North Oaks, MN (US)

(72) Inventors: Scott Dowd, Ridgewood, NJ (US); Petros Benias, Englewood Cliffs, NJ (US); Vivek Kumbhari, Atlantic Beach, FL (US)

(73) Assignee: Aurora Medical Technologies Corp, North Oaks, MN (US)

( * ) Notice: Subject to any disclaimer, the term of this patent is extended or adjusted under 35 U.S.C. 154(b) by 0 days.

(21) Appl. No.: 17/592,776

(22) Filed: Feb. 4, 2022

(65) Prior Publication Data

US 2022/0249084 A1     Aug. 11, 2022

Related U.S. Application Data

(60) Provisional application No. 63/145,708, filed on Feb. 4, 2021.

(51) Int. Cl.
| | |
|---|---|
| *A61B 17/00* | (2006.01) |
| *A61B 17/04* | (2006.01) |
| *A61B 17/34* | (2006.01) |
| *A61B 90/00* | (2016.01) |

(52) U.S. Cl.
CPC ...... *A61B 17/0401* (2013.01); *A61B 17/0469* (2013.01); *A61B 2017/00367* (2013.01); *A61B 2017/0409* (2013.01); *A61B 2017/0417* (2013.01); *A61B 2017/0456* (2013.01); *A61B 2017/0458* (2013.01); *A61B 2017/0464* (2013.01); *A61B 2017/3413* (2013.01); *A61B 17/3478* (2013.01); *A61B 2090/037* (2016.02)

(58) Field of Classification Search
CPC ............ A61B 17/0401; A61B 17/0469; A61B 17/3478; A61B 2017/00367; A61B 2017/0409; A61B 2017/0417; A61B 2017/0464
See application file for complete search history.

(56) References Cited

U.S. PATENT DOCUMENTS

| | | |
|---|---|---|
| 10,390,922 B2 | 8/2019 | Pereira et al. |
| 2001/0008971 A1 | 7/2001 | Schwartz et al. |
| 2005/0251189 A1 | 11/2005 | Saadat et al. |
| 2006/0030884 A1 | 2/2006 | Yeung et al. |

(Continued)

OTHER PUBLICATIONS

Non-Final Office Action dated Jun. 12, 2019 for U.S. Appl. No. 14/639,669 (13 pages).

*Primary Examiner* — Kelly J Bekker
*Assistant Examiner* — Lindsey R. Rivers
(74) *Attorney, Agent, or Firm* — Nutter McClennen & Fish LLP

(57) ABSTRACT

The present invention includes a single molded strip of suture anchors frangibly connected to each other that can be preloaded with a suture and then deployed at the site of use inside the body. This configuration eliminates the need to reload an anchor when multiple anchors are required. Further, this molded strip of anchors can include different variations of a suture anchor or locking device all in the same single strip. The strip would typically be molded from plastic or metal and would offer the additional advantage of being injection molded in a one piece shot which would not only save on cost per anchor but would offer assembly advantages as well.

17 Claims, 25 Drawing Sheets

(56) References Cited

U.S. PATENT DOCUMENTS

| | | | |
|---|---|---|---|
| 2008/0015566 A1* | 1/2008 | Livneh | A61B 17/320016 |
| | | | 606/37 |
| 2008/0086172 A1 | 4/2008 | Martin et al. | |
| 2008/0243148 A1 | 10/2008 | Mikkaichi et al. | |
| 2014/0031835 A1* | 1/2014 | Viker | A61B 17/42 |
| | | | 606/151 |
| 2015/0250470 A1* | 9/2015 | Vargas | A61B 17/0401 |
| | | | 606/232 |
| 2016/0324615 A1* | 11/2016 | Lund | A61F 2/0045 |
| 2018/0035997 A1* | 2/2018 | Smith | A61B 17/122 |
| 2023/0210558 A1 | 7/2023 | Dowd et al. | |

* cited by examiner

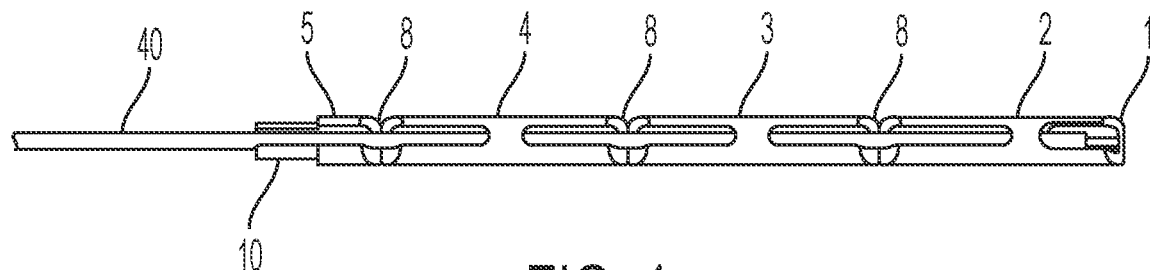
FIG. 1
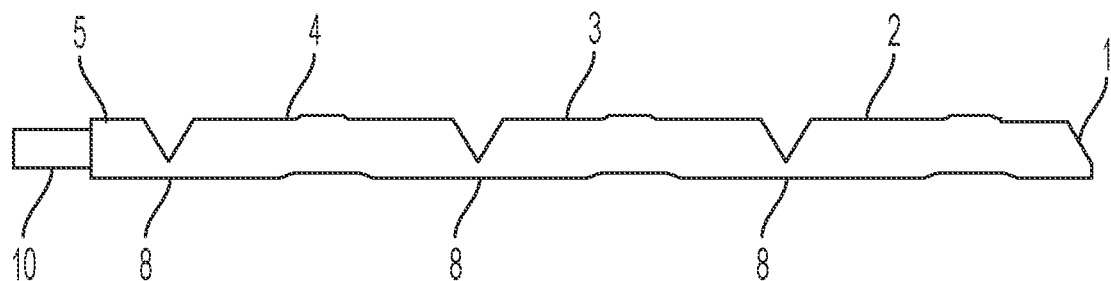
FIG. 1.1
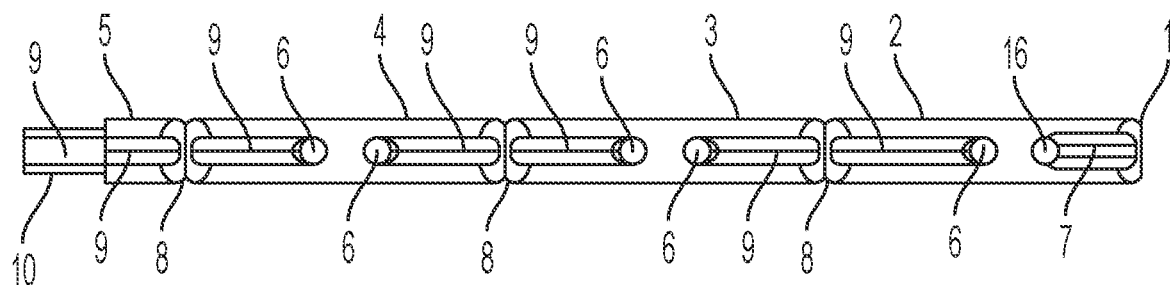
FIG. 1.2

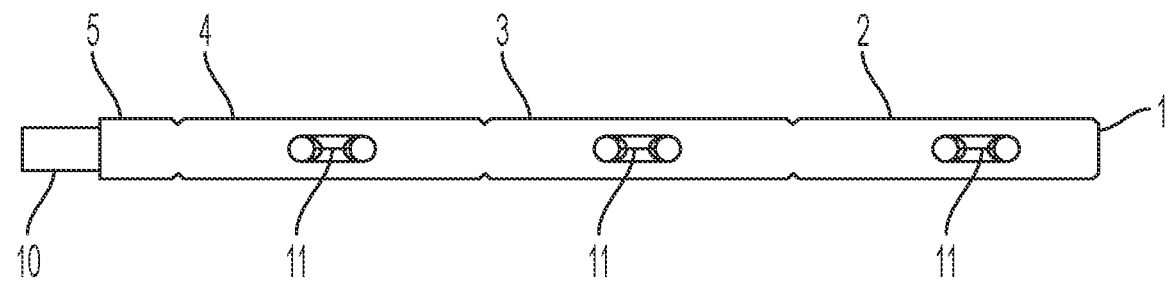
FIG. 1.3
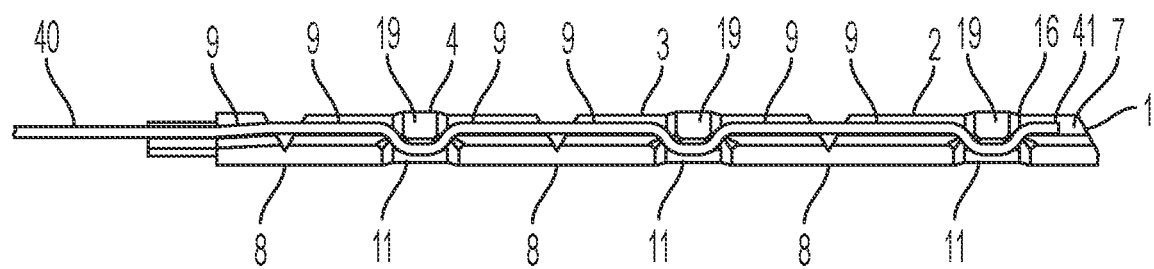
FIG. 1.4

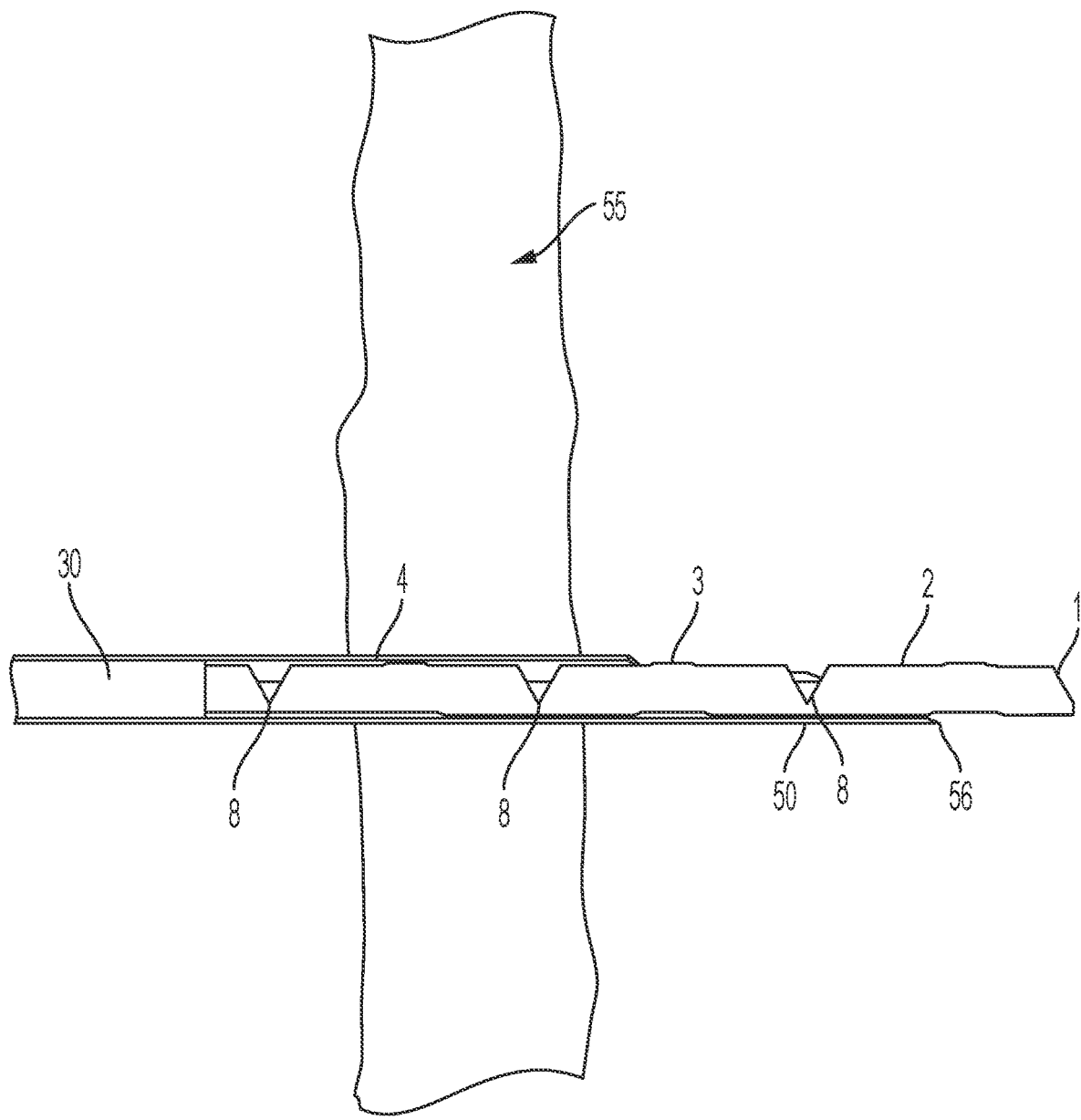
FIG. 3.1

FIG. 3.2

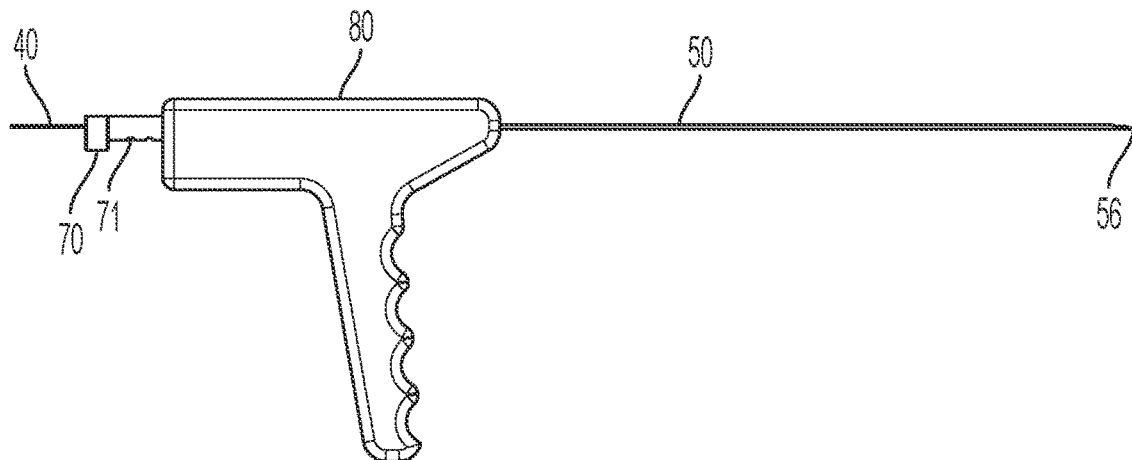
FIG. 4.1
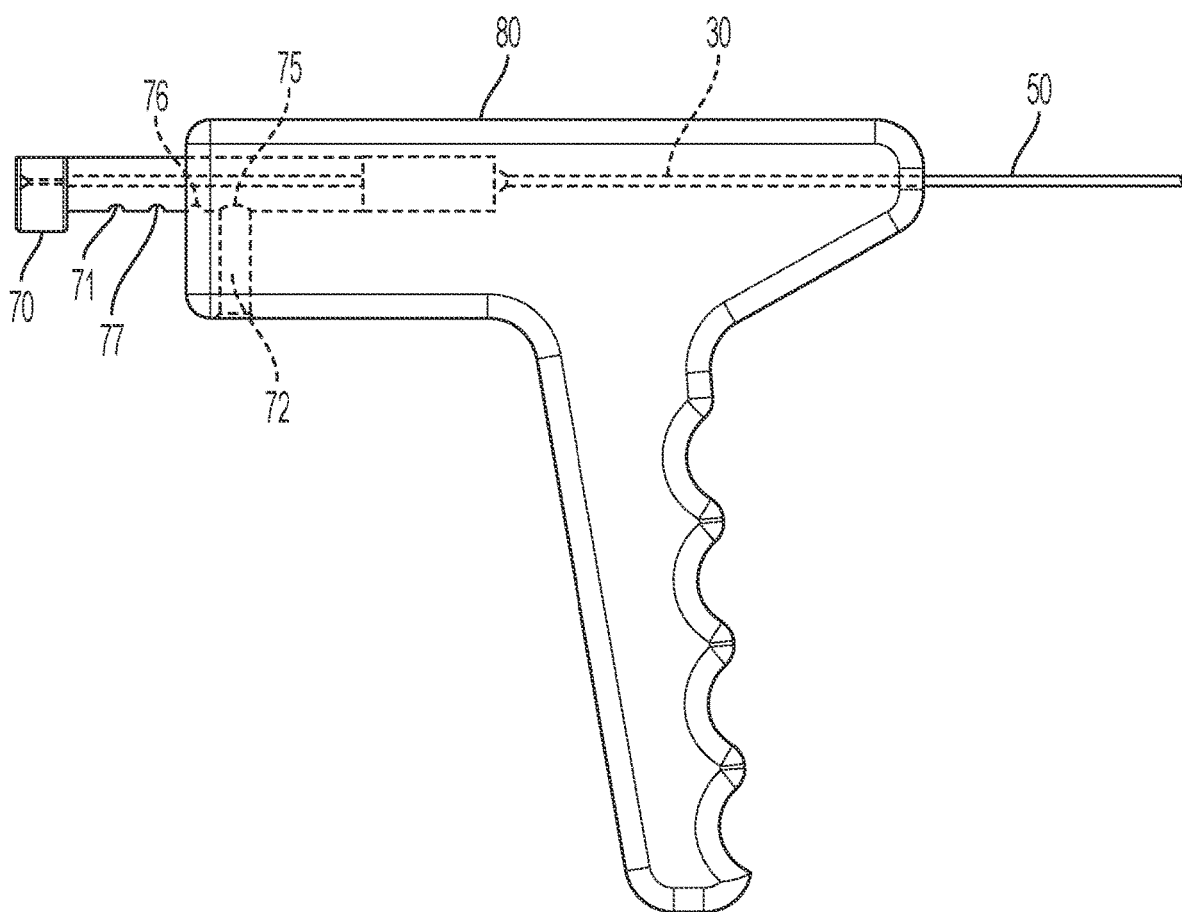
FIG. 4.2

FIG. 4.3

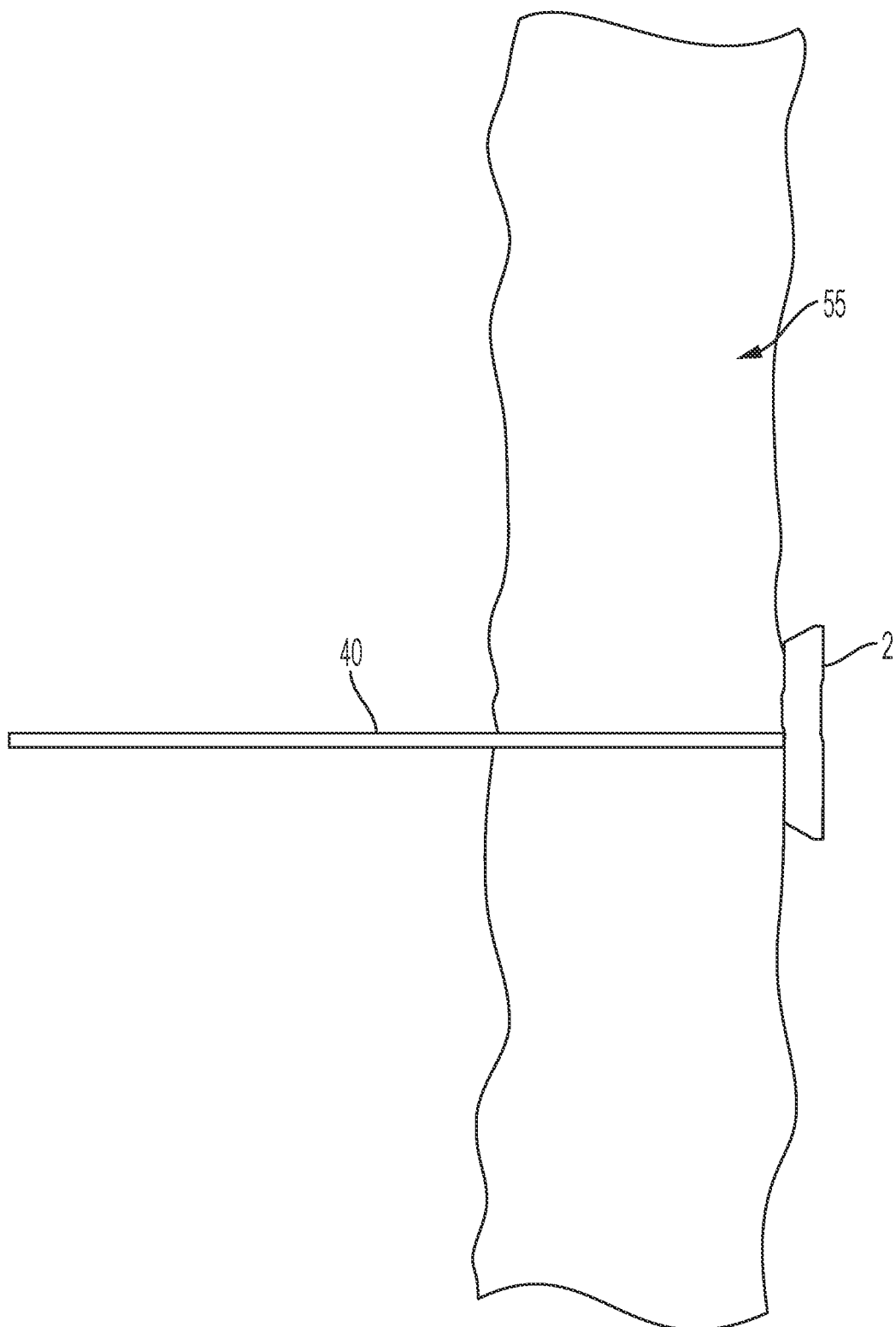
FIG. 5.1

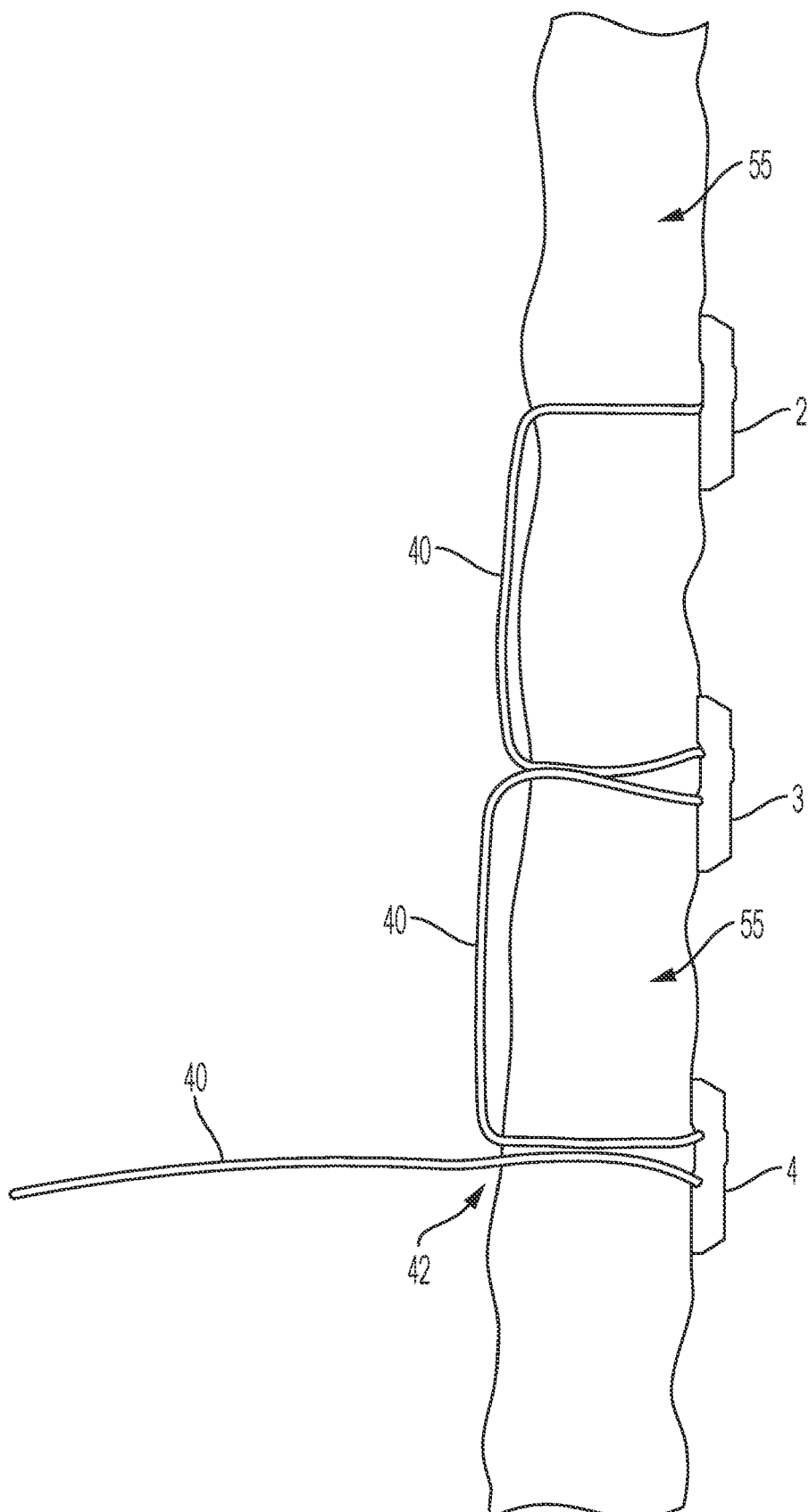
FIG. 6.1

FIG. 7.1

Insert Needle
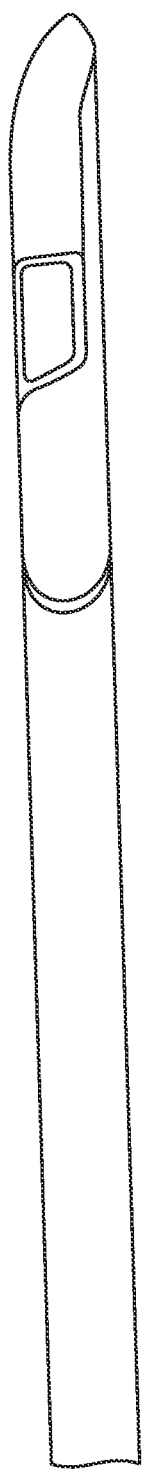
Tack will Flip and Breakaway
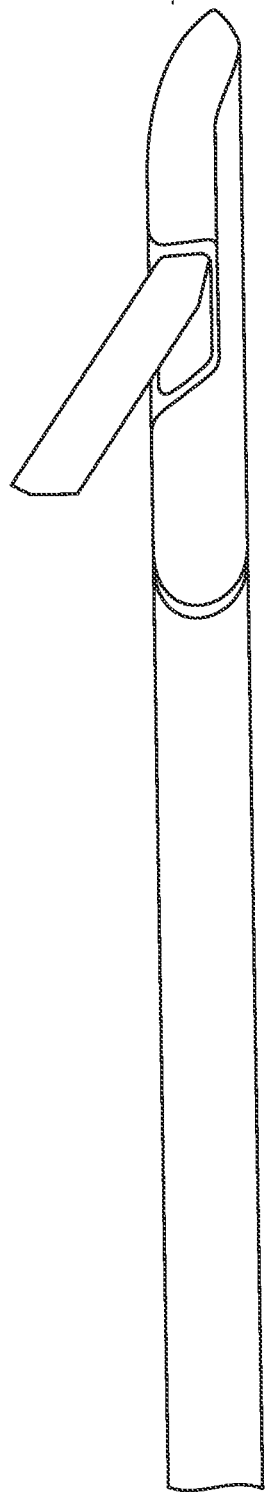
FIG. 10
FIG. 11

1. Tissue Anchors

SUTURING BREAKAWAY ANCHOR STRIP

CROSS-REFERENCE TO RELATED APPLICATIONS

The present application claims priority to and filing benefit of U.S. Provisional Patent Application No. 63/145,708, filed on Feb. 4, 2021 which is incorporated herein by reference in its entirety.

FIELD

Surgical suture anchors have historically been singular in use with most being delivered individually or gang type in a multi-fire setting. These anchors can be stainless steel, titanium, non-absorbable plastic, absorbable plastic or some hybrid of plastic and ceramic.

BACKGROUND

Techniques to improve transmural and tissue and luminal apposition are necessary for a variety of clinical indications. Tissue apposition can be performed by through-the-scope clips (TTSC), over-the-scope-clips (OTSC), and endoscopic suturing (ES) systems. These procedures lack precision, reliable transluminal suturing, and a durable and robust lumen apposition, and do not reliably achieve full thickness suturing or account for extraluminal structures. Further, they are not durable due to suture "cheese-wiring" through tissue and are too cumbersome for widespread dissemination.

Uses for transmural suturing include: gastroplasty for the treatment of overweight/obesity and its associated comorbidities such as metabolic disease; anastomotic reduction (e.g. gastric outlet and pouch reduction for the treatment of weight regain and/or dumping syndrome post gastric bypass; securing implants (e.g., self-expandable metallic stents) to the luminal wall; closure of defects involving the muscularis propria (e.g., closure of fistula/leak, after full-thickness resection of a lesion in the luminal digestive tract); anti-reflux procedure; gastropexy for sliding hiatus hernia; and tethering to the edges of a stricture with or without dilation to pry it open.

Endoscopic ultrasound (EUS) guided lumen apposition include lumen apposing metallic stents (LAMS) that have improved EUS-guided creation of an anastomosis for uses in, for example, gallbladder drainage and gastroenteric anastomosis are examples and drainage of abdominal collections. However, issues remain such as the gallbladder or small bowel is pushed away during insertion of the LAMS deployment catheter, and an insufficient length of LAMS deployment catheter is able to be inserted into the gallbladder or small bowel and the distal flange is opened between the stomach and the gallbladder or small bowel.

Flexible endoscopic methods for tissue resection are quickly gaining momentum which gives rise to a desperate need to create a robust and durable closure in an efficient, effective, durable, and safe manner. In addition, endoscopic anti-reflux therapies and endoscopic obesity therapies rely on endoscopic suturing and this must be robust and secure. There is currently no easy, safe, and reliable way to perform full thickness suturing in the gastrointestinal (GI) tract. Current technology, such as the Apollo® Overstitch, while it claims to be full thickness, often falls short or overshoots in real life practice.

The technical difficulty and invasive nature of endosurgical procedures is offset by the ability to suture and provide safe closure. There is currently no way to use imaging to guarantee transmural or full thickness placement of suture/fastener/anchor. All suturing is effectively blind, and since there is no tactile feel of the tissue being sutured, there is no ability to say that full thickness suturing is being performed reliably. There is no through the scope suturing technology that allows for full thickness plication that is currently commercially available. Over the scope attachments create maneuverability and visibility issues in real life application.

Current technologies are limited by the suture size (e.g., 2-0) due to the needle size and subsequent concerns for bleeding as vessels are not within endoscopic view during the suturing process. Current technologies are cumbersome for the average user and carry a steep learning curve and is limited to one type of suture. Nonlinear deployment makes suture management complex and novice users suffer from poorly placed sutures: these either break, become tangled, or give a false sense of secure closure.

SUMMARY

The present disclosure includes a through the scope (endoscope or echoendoscope) endoscopic or endoscopic ultrasound (EUS) and non-EUS guided tissue anchoring/suturing system that allows the user to observe full thickness tissue penetration with each pass avoiding vessels and other organs/tissues; a linear deployment that allows for increased flexibility and maneuverability; anchors that are in fact T-Fasteners which are robust on a point-to-point basis; and allows for performing transmural apposition. EUS can include echoendoscope, gastroscopes, colonoscopes, standard endoscopes and the like. These improvements provide for (i) added safety by allowing full thickness with avoidance of off-target vessels/organs/extraluminal structures, (ii) adaptability and ease of use with a straightforward deployment mechanism based on other current technology such as, for example, EUS fine needle aspiration needles (FNA), (iii) improved performance with more robust anchor design supporting a variety of suture materials, (iv) increased durability by verified transmural deployment through ultrasound capability, and (v) increased flexibility that can be used for luminal apposition and transmural apposition of tissue and fixation of objects to the lumen (stents, catheters, delivery vehicles (medications), etc.).

Specific applications of an EUS guided suturing system include EUS guided tissue apposition (luminal and transmural), luminal apposition (i.e., EUS guided tissue suturing), gastric restrictive procedures, anti-reflux procedure, gastropexy for sliding hiatus hernia, and closure of perforations. Further, transmural apposition can direct EUS drainage for infected collections, cholecystitis, and obstructive jaundice.

The present disclosure includes EUS and non-EUS guided systems using current platforms and needle-based technology. A needle-based anchor deployment system with a linear mechanism of action, which eliminates suture management problems. Tissue anchors that are deployed through the needle in a EUS guided transmural fashion. anchors that can be simple T tags or three prong anchor design (e.g., Trident). anchors that ride independently on a suture material and are then cinched at the end, for which, each fastener acts as a transmural anchor. A unique anchor retention wedge that allows suture and needle to move freely until anchor is ready to be deployed through tissue and allows for multiple anchors can be deployed in succession.

Described herein is a suture anchor system, comprising: a hypodermic needle; a frangibly assembled plurality of suture anchors; a suture connected to the frangibly assembled plurality of suture anchors; a drive hub; and a handle configured to allow manual operation of the suture anchor system. In certain embodiments, the hypodermic needle is a hollow hypodermic needle comprising an endoscopic needle or an endoscopic ultrasound needle. In some cases, the frangibly assembled plurality of suture anchors is configured to be positioned inside the hollow hypodermic needle. In one example, the drive hub is configured to drive the frangibly assembled plurality of suture anchors into a subject's flesh. In a preferred embodiment, the frangibly assembled plurality of suture anchors comprises at least a primary suture anchor. In one embodiment, the frangibly assembled plurality of suture anchors comprises suture holes and suture knot grooves configured to separate the primary suture anchor from the frangibly assembled plurality of suture anchors after insertion into a subject's flesh. In some examples, the suture anchor system is configured to insert the plurality of suture anchors into the subject's flesh as needed to suture an opening in the subject's flesh. In certain embodiments, the handle is configured to house the drive hub and hypodermic needle, and a ball plunger protrudes from the handle allowing manual operation of the suture anchor system.

Also described herein is a method of suturing an opening in a subject's flesh, comprising: preparing the suture anchor system of claim 1; deploying a primary anchor into a primary suture anchor point in a subject's flesh by inserting the hypodermic needle loaded with the frangibly assembled plurality of suture anchors into the subject's flesh; retracting the needle; moving the needle to a second suture anchor point; deploying the second suture anchor in the second suture anchor point by inserting the hypodermic needle loaded with the frangibly assembled plurality of suture anchors into the subject's flesh; repeating deploying suture anchors as needed; and cinching the suture. In some cases, deploying the primary anchor comprises driving the primary anchor into an interior side of the flesh being sutured, and once driven into the interior side of the flesh, separating the primary anchor from the frangibly assembled plurality of suture anchors. In some embodiments, retracting the needle comprises feeding the suture from the interior of the flesh to the exterior of the flesh. In one example, moving the needle to the second suture anchor point comprises determining a suture spacing sufficient to optimize healing. As such, deploying the second suture anchor comprises driving the second suture anchor into the interior of the flesh and separating the second suture anchor from the frangibly assembled plurality of suture anchors. In some examples, cinching the suture comprises pulling the suture such that the suture anchors and the suture urge the flesh together inducing healing.

Optional illustrative embodiments include:
A strip of anchors with a breakaway notch.
A molded strip of dissimilar anchors.
A method by which the anchors can breakaway or separate inside a needle or lumen.
A molded strip of anchors with a locking cinch.
A molded strip of anchors.
A strip of anchors that are manufactured in as a single monolithic piece.
A method of using anchors to oppose lumens.
A method of using anchors to reduce the volume of an organ (stomach).
A method of securing objects to the luminal wall.
A method of inducing weight loss and improvement in metabolic profile with the reduction of volume of an organ (e.g., stomach).
A method to secure a luminal wall.
A method of securing one structure to another structure or one lumen to another lumen.
A method of opposing the bile duct to the luminal gastrointestinal tract under EUS guidance.

Covered embodiments of the invention are defined by the claims, not this summary. This summary is a high-level overview of various aspects of the invention and introduces some of the concepts that are further described in the Detailed Description section below. This summary is not intended to identify key or essential features of the claimed subject matter, nor is it intended to be used in isolation to determine the scope of the claimed subject matter. The subject matter should be understood by reference to appropriate portions of the entire specification, any or all drawings, and each claim.

BRIEF DESCRIPTION OF THE DRAWINGS

FIGS. 1-1.4 schematically show a single molded strip of anchors according to an illustrative embodiment.

FIG. 10 is a digital image illustrating a deployment procedure according to an illustrative embodiment.

FIG. 11 is a digital image showing the anchor strip in a needle during deployment according to an illustrative embodiment.

DETAILED DESCRIPTION

The present invention includes a single molded strip of anchors (FIG. 1) frangibly connected to each other that can be preloaded with a suture and then deployed at the site of use inside the body. This configuration eliminates the need to reload an anchor when multiple anchors are required. Further this molded strip of anchors can include different variations of a suture anchor or locking device all in the same single strip (see FIGS. 1.2, 1.3). The strip would typically be molded from plastic or metal and would offer the additional advantage of being injection molded in a one piece shot which would not only save on cost per anchor but would offer assembly advantages as well.

The new design would be loaded with a single suture strand and a knot (FIG. 1.4) placed at the distal tip of the anchor strip. This preloaded anchor strip would then be assembled into a delivery needle (FIG. 2) with the distal tip of the anchor strip kept behind the distal needle tip. To deploy the first distal anchor place the needle through the tissue and advance the anchor strip so that one anchor segment is exposed outside of the needle (FIG. 3). Then by pulling on the proximal end of the suture (FIG. 4), the first anchor segment will snap off and separate from the anchor strip causing it to toggle (FIG. 5) and lock into or behind the tissue. The needle is then repositioned to the next location and repeat the procedure again (FIG. 6) for as many times as the anchor strip will allow. The new design includes three anchors molded into a single strip. However, any number of anchors can be molded together in this fashion.

Figure 7:
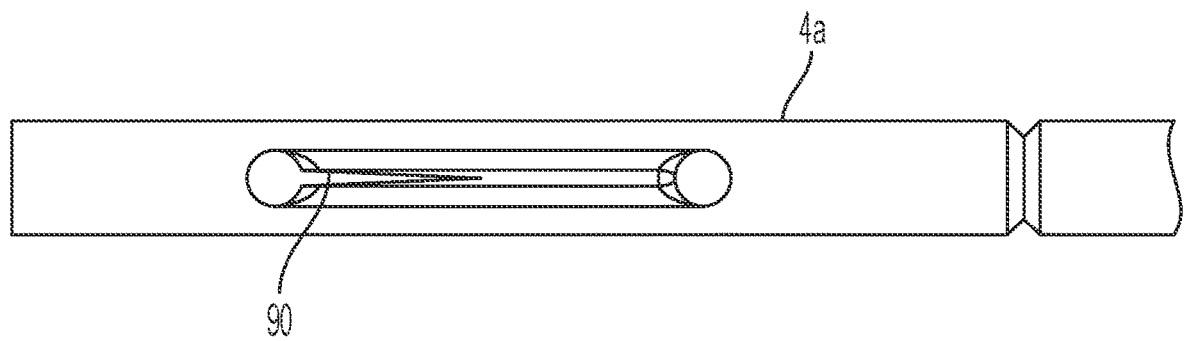
FIGS. 7-7.1 schematically show a cinch anchor according to an illustrative embodiment.

When the last anchor segment has been reached it can be deployed in the same manner. However, after it is deployed the suture is pulled taut which creates a "purse string" closure of all of the previously deployed anchors. At this time a locking cinch anchor type device can be used to hold the suture and lock it in place. Alternately, the final anchor in the strip anchor could contain a locking cinch type feature anchor (FIG. 7) which locks the suture when pulled taut. The suture can then be cut with another instrument. This final anchor locking cinch is achieved by utilizing the locking "v" in the final proximal anchor segment (FIG. 7). The "v" increases the locking of the suture the more the suture is pulled taut into the v-shaped grooved.

Another variation of the above invention would be to have the anchors individually separate inside the needle before exiting. This would be achieved by placing a slight curve into the distal tip of the needle so that when the anchor strip is pushed forward into the curve, the most distal anchor snaps off or separates just before exiting the needle tip. Once the anchor has exited the needle it is free to toggle and lock into or behind the tissue. The remainder of the anchors in the molded strip remain connected until the procedure is repeated.

Figure 3:
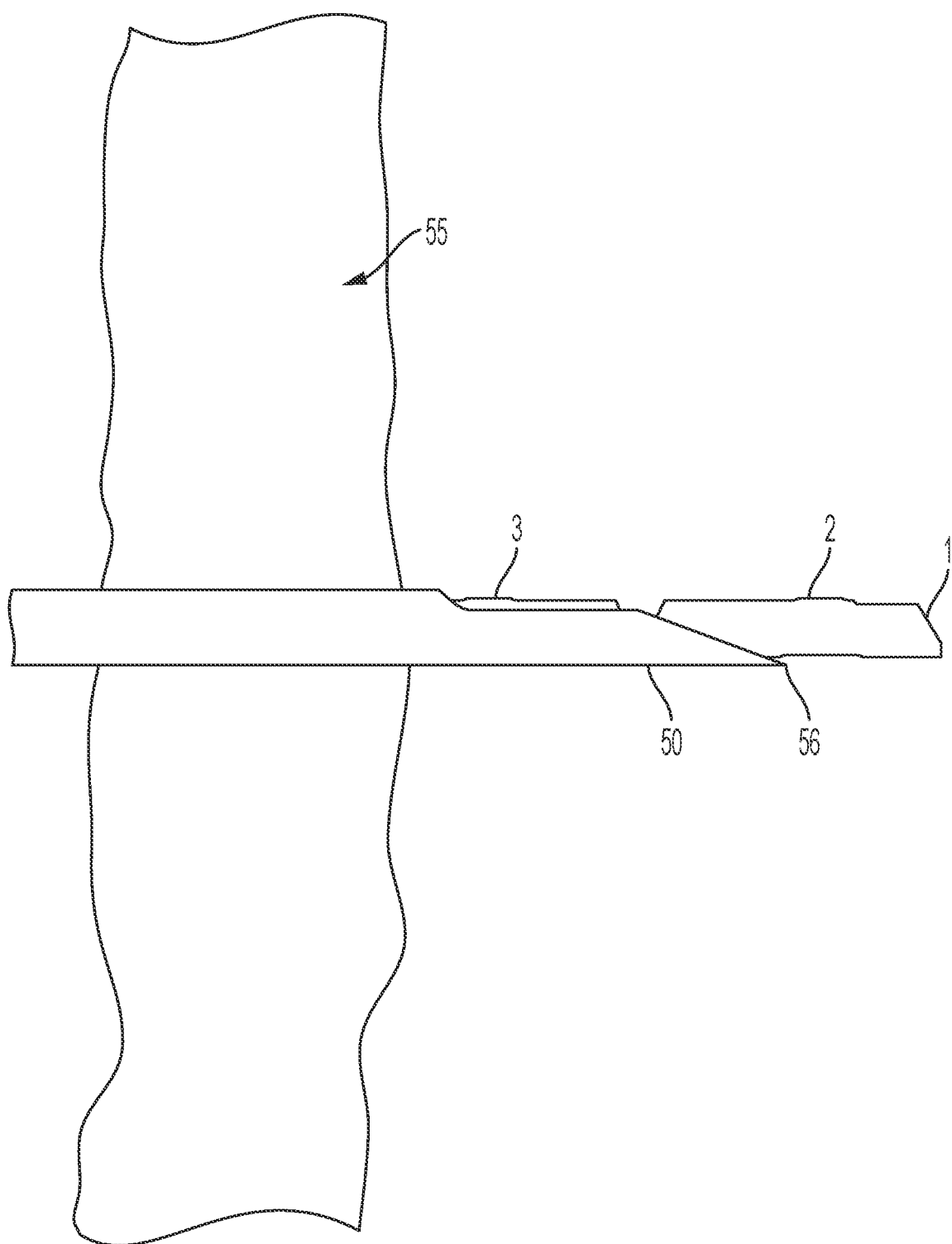
FIGS. 3-3.2 schematically show the anchor strip ready for deployment according to an illustrative embodiment.
Figure 4:
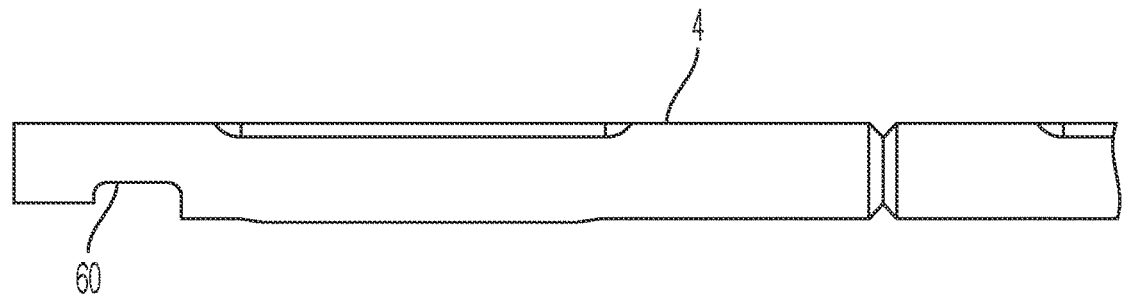
FIGS. 4-4.3 schematically show a deployment system according to an illustrative embodiment.
Figure 4:
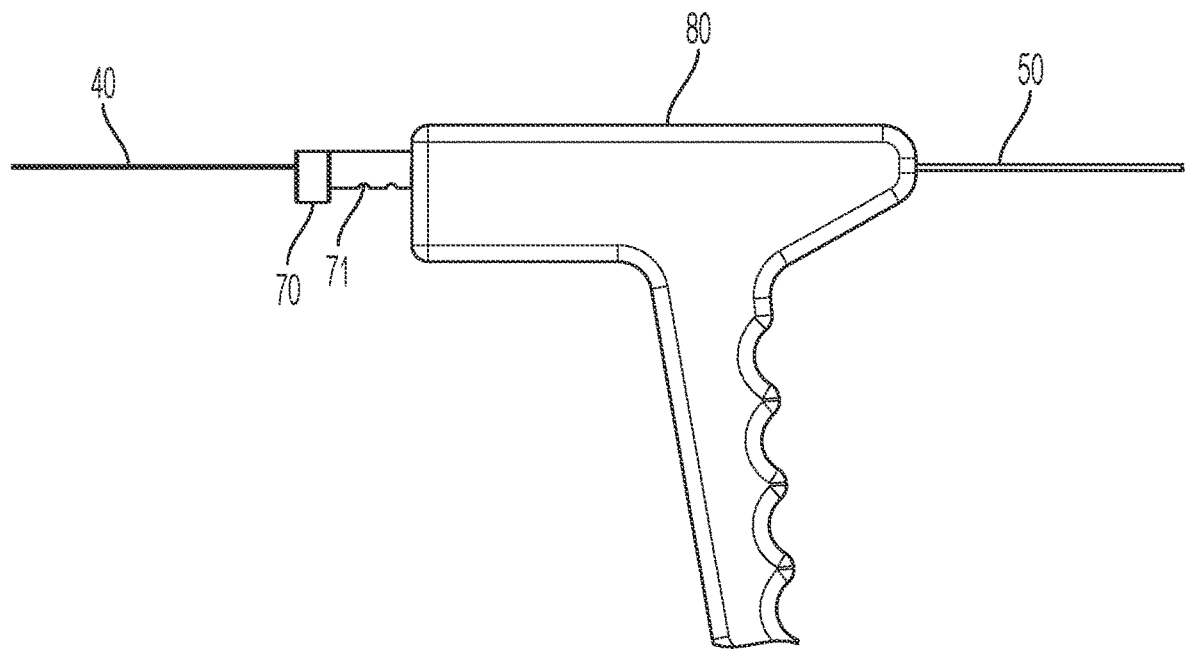

The anchor strip is advanced or driven by a pusher (FIG. 3) which holds the proximal end of the tack strip via a press fit portion. This pusher is then connected on the proximal end to a drive hub (FIG. 4). The Pusher is made from a stainless tube which allows a suture to be placed internally with the suture continuing to pass through the handle and drive hub.

Alternately (FIG. 3.2) the anchor strip could be connected to a pusher via a notch to connect or mate with the proximal end of the anchor strip.

The handle contains a drive hub (FIG. 4) portion which is connected to the proximal end of the pusher, so that when the drive hub is pushed forward the anchor strip is advanced. The pusher hub has detents that allow for it to stop at a predetermined location in the handle. These detents mate with a ball plunger assembled in the handle. Further, the distance between the detents is equal to the length of the anchors. This will allow for each anchor to be advanced the set amount until the final anchor is reached. This is also depicted by indicator numbers which show the anchor number before advancing.

FIGS. 1-1.4 are a series of diagrams of the anchor strip, showing a total of three anchors connected to each other according the invention.

FIG. 1 shows an isometric view of the anchor strip 1 with a suture attached 40. A key feature of the invention is the ability to manufacture the anchor strip 1 in a single piece, typically via molding or 3D printing. The advantages of the single piece include: cost savings of molding one piece; control and orientation of the anchors; ease of and cost saving for assembly; and simplicity of the design without the need for additional design features to orient and hold the anchors in place.

FIG. 1.1 depicts a side view of anchor strip 1 which includes three anchors 2, 3, 4 and a holder 5 all connected by notches 8. Anchor 2 is the initial primary anchor 2 followed by secondary anchors 3 and 4.

FIG. 1.2 shows a top view of anchor strip 1 with suture holes 6 and suture knot groove 7 with suture hole 16 which is where the knot is placed. It also depicts suture grooves 9. Knot groove 7 is larger than suture slots 9 to allow for the increased size associated with a knot.

FIG. 1.3 shows a bottom view of anchor strip 1 with a connector end 10 that connects to a pusher 30 via a press or crimped fit. The pusher 30 will drive the entire anchor strip 1 through the needle tube and exit into or behind the tissue. It also shows suture grooves 11.

FIG. 1.4 shows a section view pf the anchor strip 1 and suture 40 threaded through hole 16 with suture knot 41. The suture 40 is threaded or woven through the entire anchor strip 1 weaving in and out of suture holes 6 and suture grooves 9 and 11. Another key feature of the invention is the slots 9 and 11 for the suture 40 are offset from each other to allow for an increased cross section 19. If suture 40 were placed in a straight line through the anchor strip 1, the cross section 19 would be approximately one half of the thickness and could fail when the suture 40 is pulled tight after deployment. Failure would be by the suture either pulling or sawing through the cross section.

Figure 6:
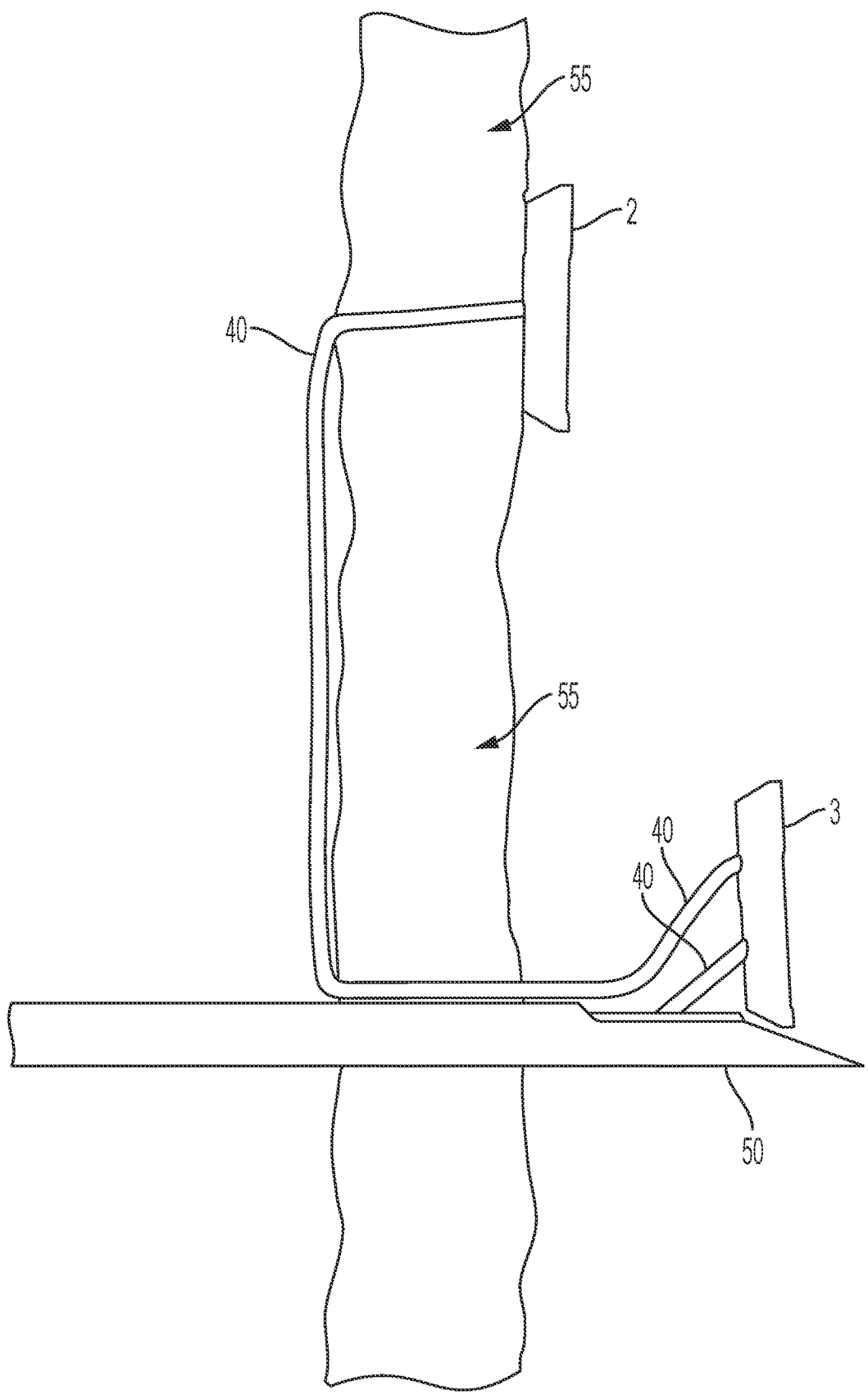
FIGS. 6-6.1 schematically show a plurality of anchor strip placements according to an illustrative embodiment.

Previous toggling type devices and conventional thinking would have the suture placed in a straight line through the anchor leaving a smaller cross section for the suture to slide on after deployment. Typical toggling type devices would be manufactured with a tube or rod with a hole drilled through it. This cross section is required so the suture 40 can slide and hold onto the anchors as seen in FIG. 6.1 and is especially necessary for anchors 3 and 4 as they require sliding of the suture 40 through the devices.

Figure 2:
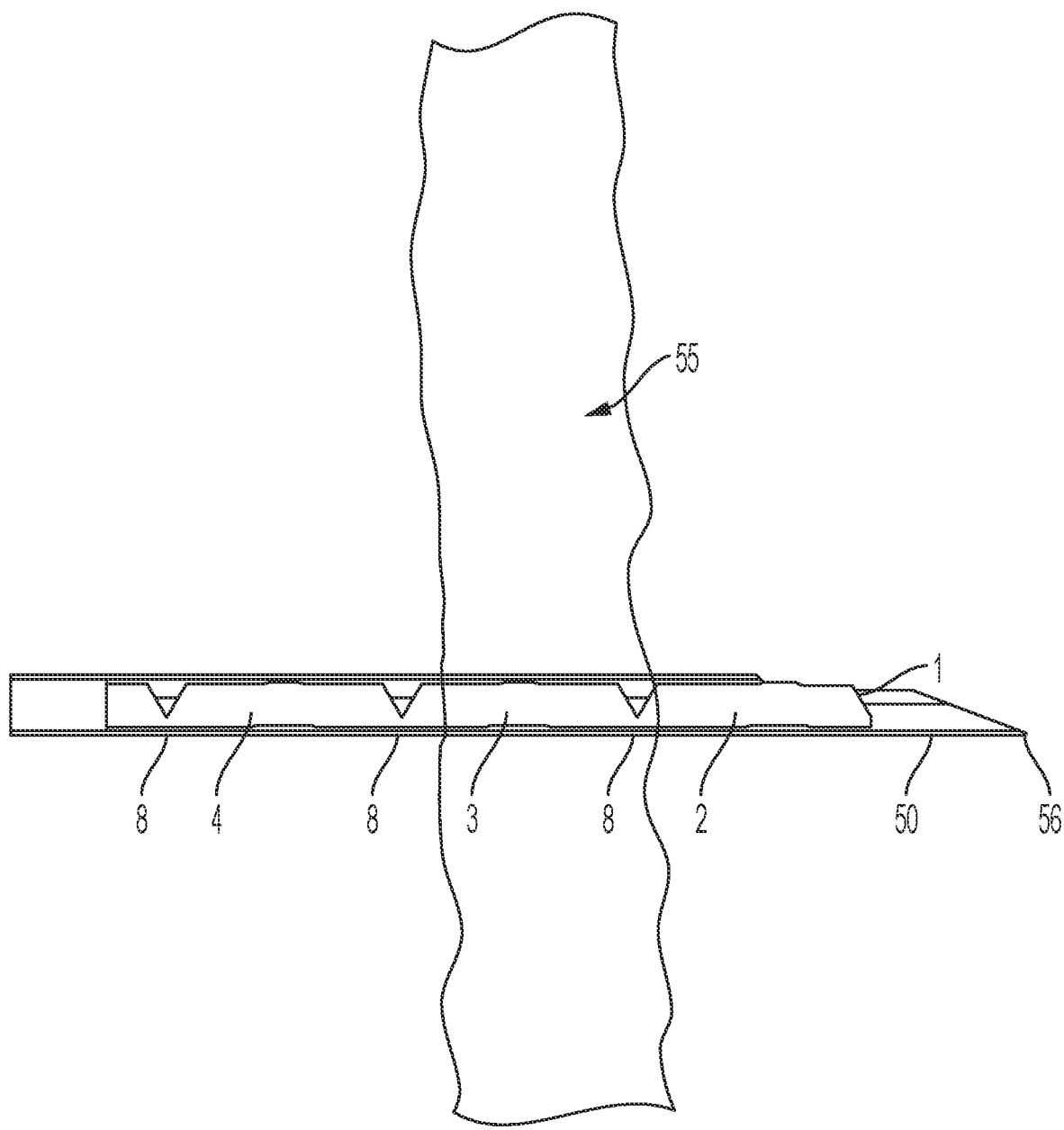
FIG. 2 schematically shows a side view of an anchor strip according to an illustrative embodiment.

FIG. 2 shows a side view of anchor strip 1 loaded into sectioned needle 50 passed through tissue 55 and ready for delivery. Yet another key feature of the invention is the control the user has of all the anchors 2, 3, and 4 due to rigid connections, notch 8, between each anchor. This control is necessary for the orientation of each anchor so that it toggles correctly in an upright position, with the suture able to freely move out of the anchor slot 9. If the orientation was not in the upright position and the suture not able to freely move out of the slot, the anchor would not toggle correctly causing pullout of the device from tissue 55.

Another control feature is linear movement inside the needle. If the anchor were not connected to a drive device, it could fall out of the needle and into the body. Additional design features are typically necessary to prevent this fall out including a detent of some sort to the needle.

It should be noted the needle 50 could also be deployed mid substance to tissue 55 instead of through the tissue 55.

FIGS. 3-3.2 are of the anchor strip advanced and ready to deploy. Also shows an alternative connection or mate with the pusher tube.

FIG. 3 shows anchor strip 1 advanced beyond needle 50, with anchor 2 protruding past needle tip 56.

FIG. 3.1 shows anchor strip 1 with anchor 2 advanced by pusher 30 beyond sectioned needle 50 and needle tip 56. Pusher 30 is connected to drive hub 70.

FIG. 3.2 shows anchor strip 1 could be connected to a pusher via a notch 60 to connect or mate with the proximal end of the anchor 4.

FIGS. 4-4.3 are views of the handle, drive hub and ball plunger.

FIG. 4 shows the handle 80 with drive hub 70 and proximal end of the suture 40. Also shows detents 71.

FIG. 4.1 shows the entire device.

FIG. 4.2 shows a hidden view assembly with ball detent 72 that engages with detents 71. There are a total of four detents. It also depicts pusher 30 that is connected to drive hub 70 going through handle 80 and through needle 50.

FIGS. 4.2 and 4.3 show indicators 73 on drive hub 70. These indicator numbers coincide with the four detents. When indicator "0" is shown, this is for the first or distal most detent 75 that is engaged with ball plunger 72 and with anchor 2 being behind the needle tip 56 as shown in FIG. 2. Indicator "1" is for the second detent 76 with anchor 2 ready for deployment and now protruding past needle tip 56 as shown in FIG. 3. In the indicator "1" position the "0" will no longer be visible. The anchor 2 will be the first anchor ready to deploy and coincides with the indicator "1" as the first anchor for deployment. Indicator "2" is for the next detent 77 and second anchor which places anchor 3, now protruding past needle tip 56, in the same previous place as anchor 2. Each successive indicator number would advance the next anchor ready for deployment.

Figure 5:
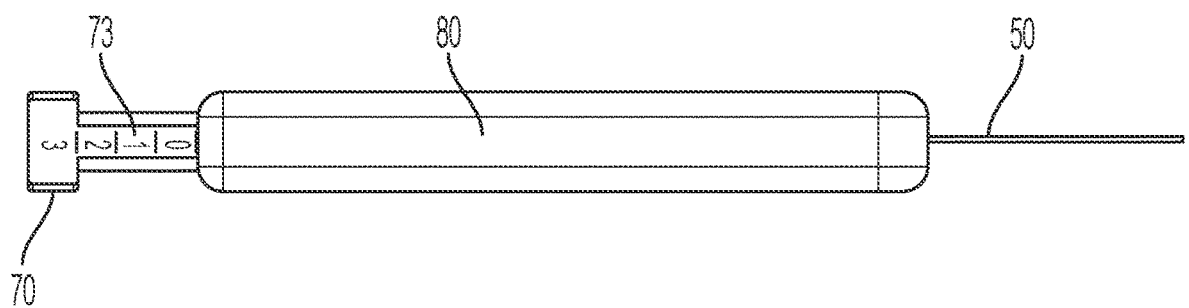
FIGS. 5-5.1 schematically show the anchor strip during deployment according to an illustrative embodiment.
Figure 5:
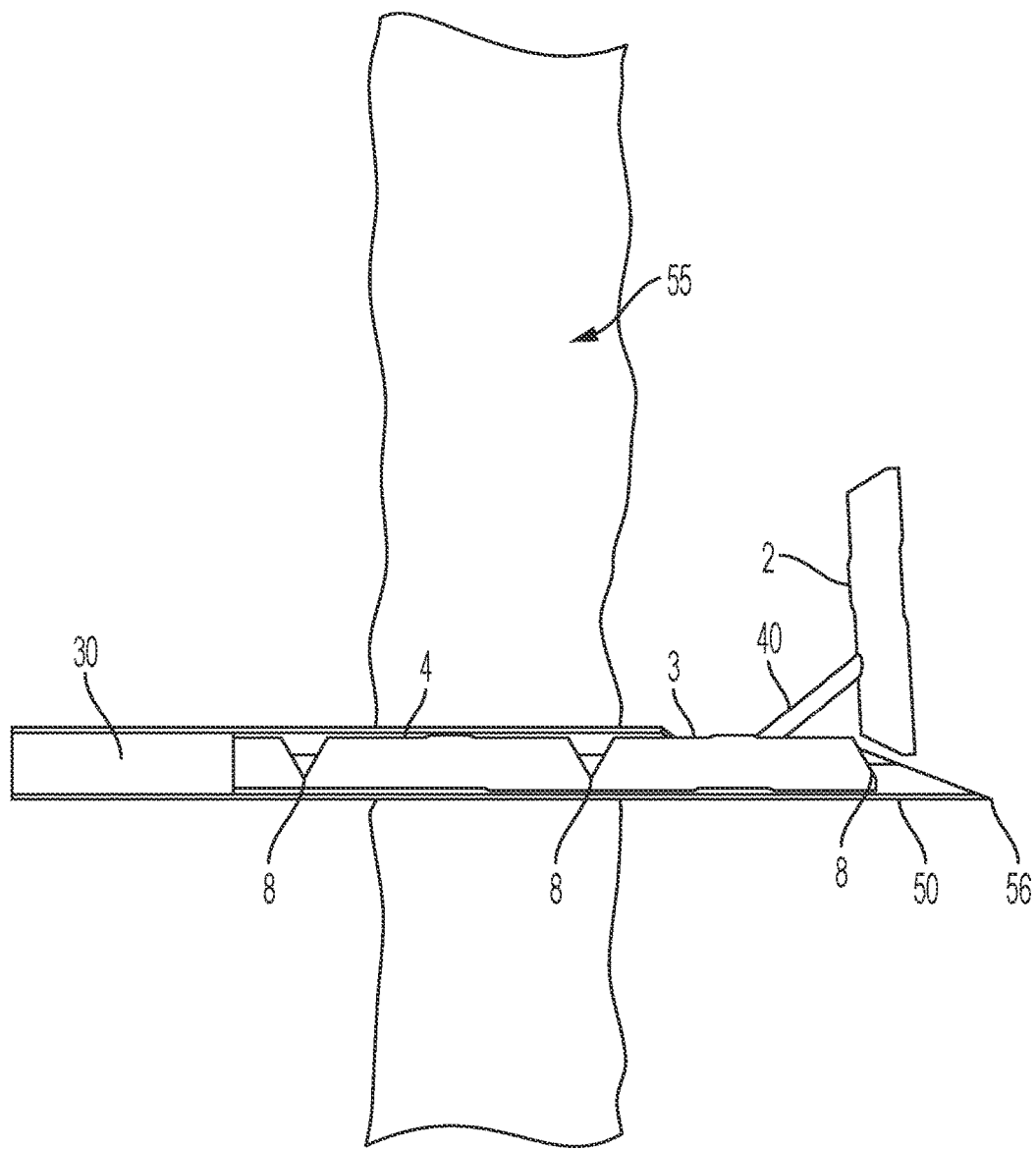

FIGS. 5-5.1 are views of anchor 2 being deployed.

FIG. 5 shows primary anchor 2 separated from the anchor strip 1 and behind tissue 55. The primary anchor 2 will separate via notch 8 and toggle when advanced with pusher 30 followed by pulling the suture 40. Suture 40 allows a connection of the primary anchor 2 and the now shortened anchor strip which now consists of two anchors (anchors 3, 4). Suture 40 is fixed to primary anchor 2 by knot 41 and cannot slide. Yet another key feature of the invention is the breakaway tab 8 which allows controlled separation of the anchor. This controlled separation when pulling of the suture, is key to flipping or toggling the anchor. Current toggling-type anchors do not consistently flip especially in mid-substance type environments resulting in pullout of the anchor device.

FIG. 5.1 shows primary anchor 2 toggled and behind tissue 55. This is achieved by removing the needle 50 from the tissue 55 and pulling on the suture 40 which locks behind tissue 55.

FIGS. 6-6.1 are views of multiple anchor placements.

FIG. 6 shows anchor 2 delivered, toggled, and locked behind tissue 55 with anchor 3 having been delivered, toggled, and ready to be locked. After needle 50 is removed and when anchor 3 is locked behind tissue 55, suture 40 can be pulled taut being free to slide within anchor 3 which allows for tightening between anchors.

FIG. 6.1 shows anchors 2, 3, and 4 deployed behind tissue 55. The free leg of suture 40 can be pulled taut with suture 40 being free to slide within anchors 3 and 4. After tightening, a cinch anchor similar to the Apollo® type cinch (Apollo Endo-surgery of Austin, Texas, USA), it can be applied to suture 40 in the area of 42.

FIG. 7 shows the cinch anchor 4a which would be in place of anchor 4. V-Groove 90 is shown for the suture (not shown) to wedge into. This cinch anchor would be in place of the known Apollo® type device and placed on the distal side of tissue 55 as shown in the anchor 4 placement. The suture 40 would then be cut in area 42 with a suture cutting instrument.

FIG. 7.1 shows cinch anchor 4a which would be in place of anchor 4. V-Grooves 90 and 91 are shown for the suture (not shown) to wedge into.

In alternate embodiments according to the present disclosure, the currently available forward viewing linear array echoendoscope is inserted into the patient as per routine and known methods. A location is chosen for the first full thickness anchor deployment. Endoscopic ultrasound is used to identify whether there are any major vessels or adjacent structures, and if so, the scope can be adjusted accordingly.

EUS allows one to observe full thickness penetration with each pass avoiding vessels and other organs, while linear deployment allows for increased flexibility and maneuverability. anchors are in fact T-Fasteners or similar which provide a more robust anchor on a point to point basis. Options for suture material are no longer limited by the device allowing for more robust applications. EUS guided approach also allows us to perform transmural apposition which has never been previously performed.

The needle 50 is loaded through the working channel of the echoendoscope and is locked into place at the biopsy valve with a Leuer lock mechanism as is standard for all EUS needles. The needle will be pre-loaded with the primary tissue anchor which will be positioned behind the retaining wedge of the needle tip. The suture is running through the center of the needle and exits at the back end of the handle. In addition, an open design needle stylet is positioned behind the tissue anchor and alongside the suture such that pushing it into the down position would effectively push the anchor out of the needle.

Figure 8:
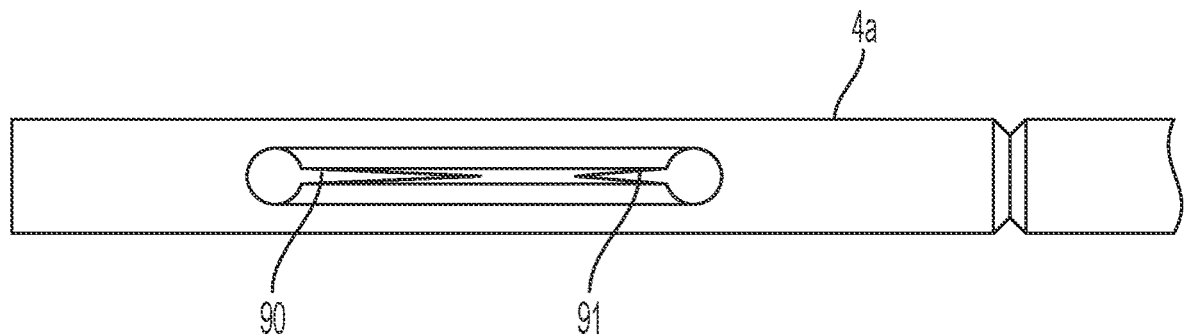
FIG. 8 is a digital image showing an anchor strip in a needle according to an illustrative embodiment.
Figure 8:

FIG. 8 is a digital image (photograph) showing the anchor 4 protruding from the needle 50. The anchor 4 is loaded with a suture 40. The anchor 4 includes v-grooves 90 in which the suture 40 is mounted.

Figure 9:
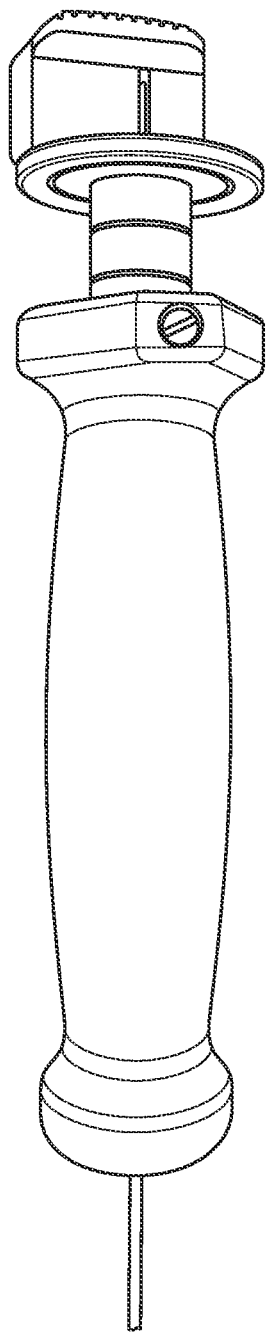
FIG. 9 is a digital image showing a drive hub according to an illustrative embodiment.

FIG. 9 is a digital image of the drive hub 70 and indicators 73. The needle 50 is protruding from the handle 80.

Figure 12:
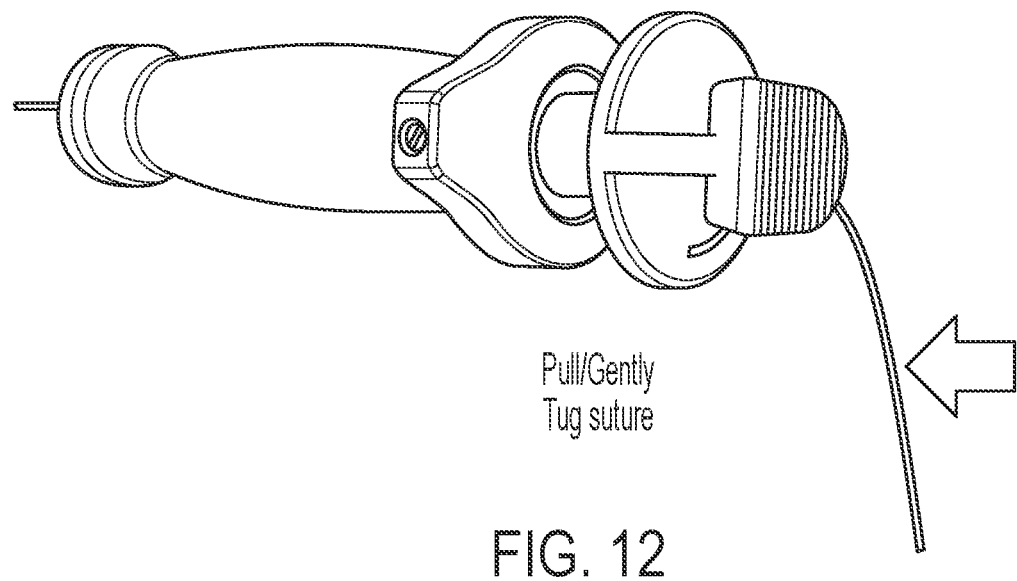
FIG. 12 is a digital image showing the drive hub during deployment according to an illustrative embodiment.
Figure 13:
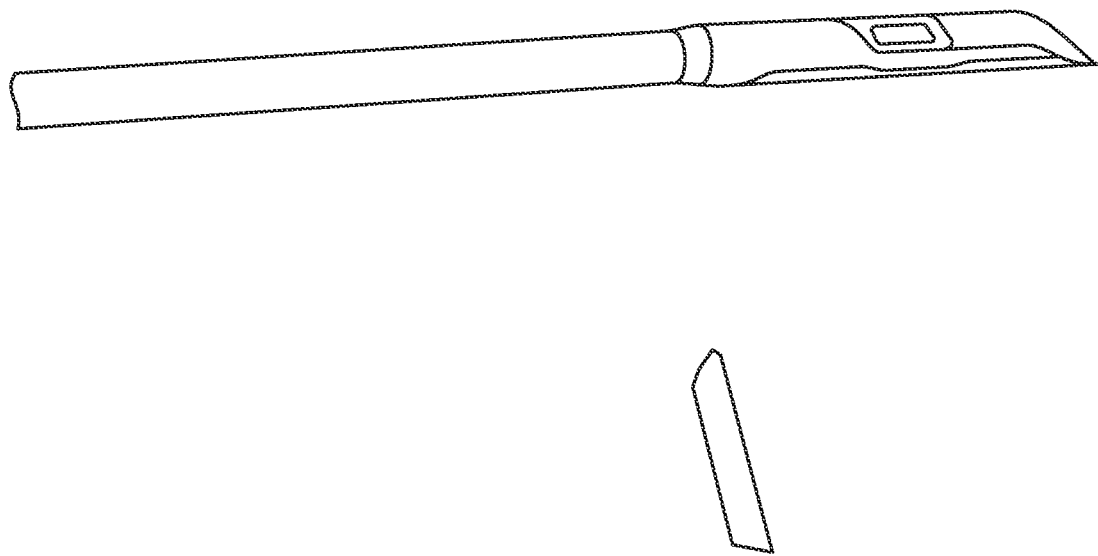
FIG. 13 is a digital image showing the anchor strip deployed from the needle according to an illustrative embodiment.
Figure 14:
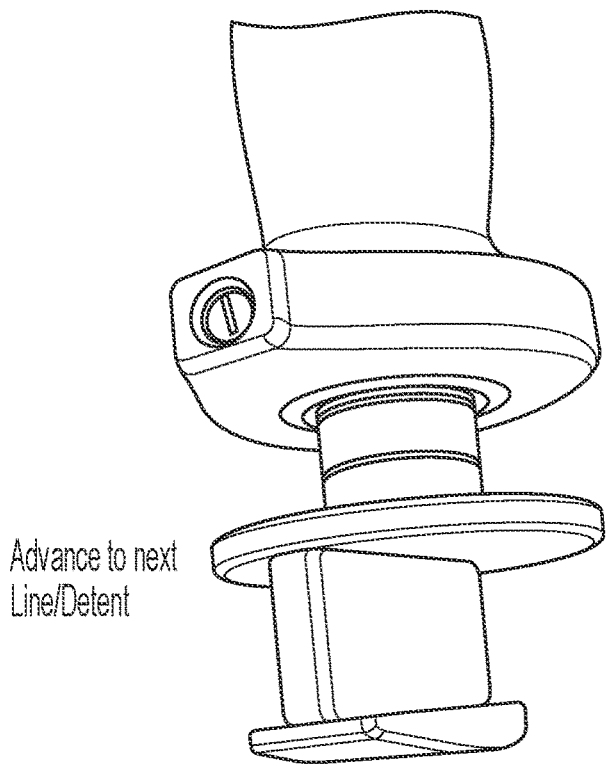
FIG. 14 is a digital image showing the drive hub during deployment according to an illustrative embodiment.
Figure 15:
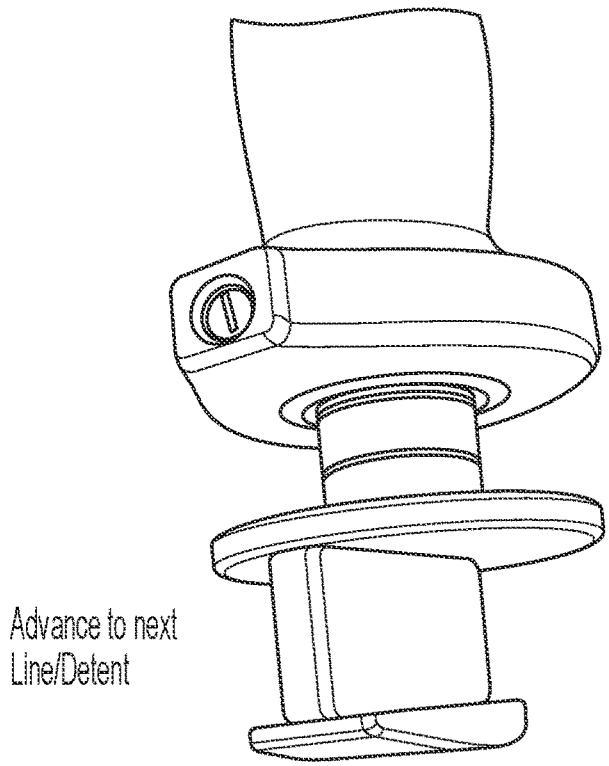
FIG. 15 is a digital image showing the drive hub during deployment according to an illustrative embodiment.

FIGS. 10-15 are digital images illustrating a deployment procedure. FIG. 10 shows the anchor strip 1 mounted in the needle 50 ready for insertion into a subject. FIG. 11 shows the anchor 2 separating from the anchor strip 1. The orientation of the anchor 2 will secure the anchor 2 within the flesh of the subject. FIG. 12 illustrates the action employed to the drive hub 70 to perform the suturing. When an anchor 2 is deployed, the handle 80 of the apparatus is pulled away from the subject, extracting the needle 50 from the subject's flesh. The force of the pull is necessarily insufficient to extract the anchor 2 from the subject. FIG. 13 demonstrates the anchor 2 separating from the needle 50 and anchor strip 1 with the suture 40 remaining attached. In an actual deployment, the anchor 2 remains within the flesh of the subject anchoring the suture 40. The apparatus is then moved to the next anchor location and the needle 50 is inserted into the flesh at the next anchor position and the drive hub 70 is advanced to the next indicator 73. FIG. 15 indicates that the deployment procedure is repeated as necessary to complete the suturing process.

Following deployment of the primary anchor, the needle is retracted and the echoendoscope is pulled back from the site of primary anchor deployment. At this time the suture line continues to run through the center of the needle and out of the needle tip. A secondary anchor (can also be preloaded) is loaded by pulling out the stylet, threading the anchor over the suture and using the stylet to push the anchor to the needle tip. The anchor automatically stops at the retaining wedge and this allows the scope and suture to move independently of the needle and anchor.

Then a second site of anchor insertion is chosen and the above steps are repeated. The secondary anchor is deployed transmurally. This is repeated until a sufficient number of anchors are deployed transmurally to provide adequate apposition of tissue upon cinching. Cinching is performed by removing the needle form the endoscope channel and running a cinch over the suture. Alternately, a removeable inner needle design would allow the internal stylet to be removed while maintain the needle sheathe and handle in position. The cinch is pushed against the tissue and the suture is pulled against the cinch bring all tissue anchors together. The suture and anchors move independently from one another until they are tightly cinched. The procedure is repeated with a new primary anchor, followed by secondary tissue anchors and a second cinch to perform a second running transmural application.

There will be a primary tissue anchor and secondary anchors. The primary anchor is the anchor that is used for the first transmural pass. The primary anchor is unique in that it is fixed to the suture. In the secondary anchors, the suture is free to pass through the anchor as the user cinches the stitch. Along with the final cinch, the primary anchor is crucial for pulling together all the intervening tissue. The anchors and/or anchor strip can be a simple bar design, wherein each anchor hinges once it's transmural to act as a T Tag. Alternately a more complex design can be conceived of shaped nitinol such that once the anchor is pushed out of the needle the back half forms a Y shape. The suture is coupled with the anchor, unlike in the secondary anchors where the anchor runs freely over the suture. The suture attaches to the anchor in the midpoint so that once it is cinched there is equal distribution of pressure.

Secondary anchors are unique and allow for this device to deploy multiple such anchors thereby apposing multiple points of tissue. They are made of the same material and dimensions as the primary anchor but have been shaped so that the suture runs through its center at the mid-point. This allows the anchor to hinge, and once it's pushed through the wall of the tissue the anchor does not allow the suture to pull through. A simple design can be conceived as in A, however more elaborate designs are also possible. One such design is a tightly wound coil that is pushed through the needle on deployment. As the needle and suture pulls back, owing to the length of the coil, it will not be able to pull out, but rather "bunch up" forming a knot. This particular design may be easier to deploy when the scope and needle position provide increased resistance due to bends and tortuosity.

Figure 16:
FIG. 16 schematically shows a top view of a needle according to an illustrative embodiment.
Figure 17:
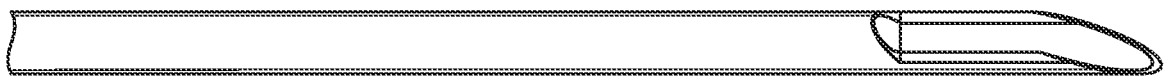
FIG. 17 schematically shows a perspective view of a needle according to an illustrative embodiment.
Figures 18, 19:
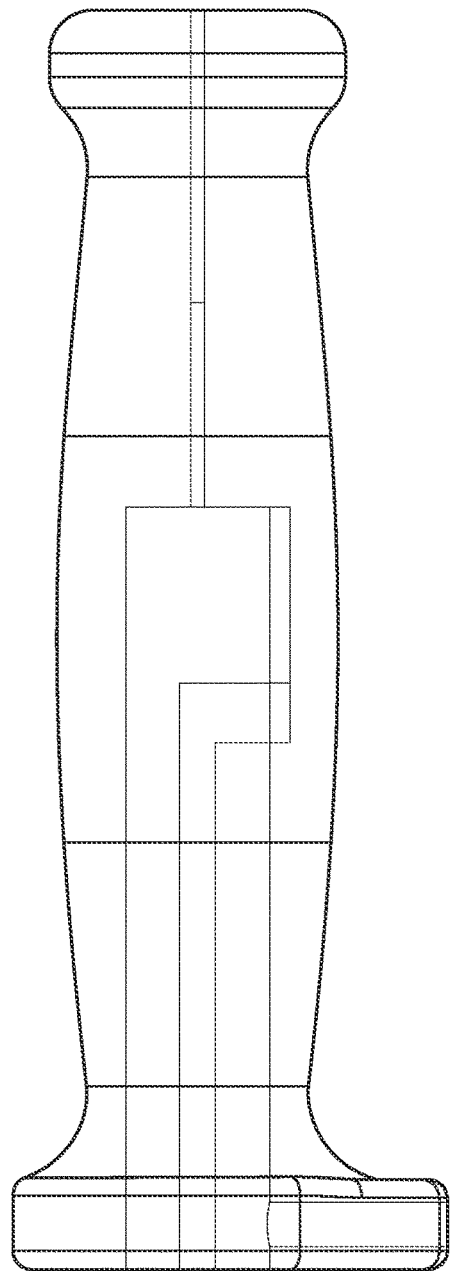
FIG. 18 schematically shows a side view of a needle according to an illustrative embodiment.
FIG. 19 schematically shows a side view of a deployment system according to an illustrative embodiment.

FIG. 16 schematically shows the endoscopic needle 50. The needle tip 56 is a tapered shape configured to house the anchor strip 1 before deployment. FIG. 17 schematically shows a perspective view of the needle 50 detailing the tapered tip 56. The taper facilitates insertion into the flesh of a subject. FIG. 18 schematically shows a side view of the needle 50, further illustrating the tapered tip 56.

Figure 20:
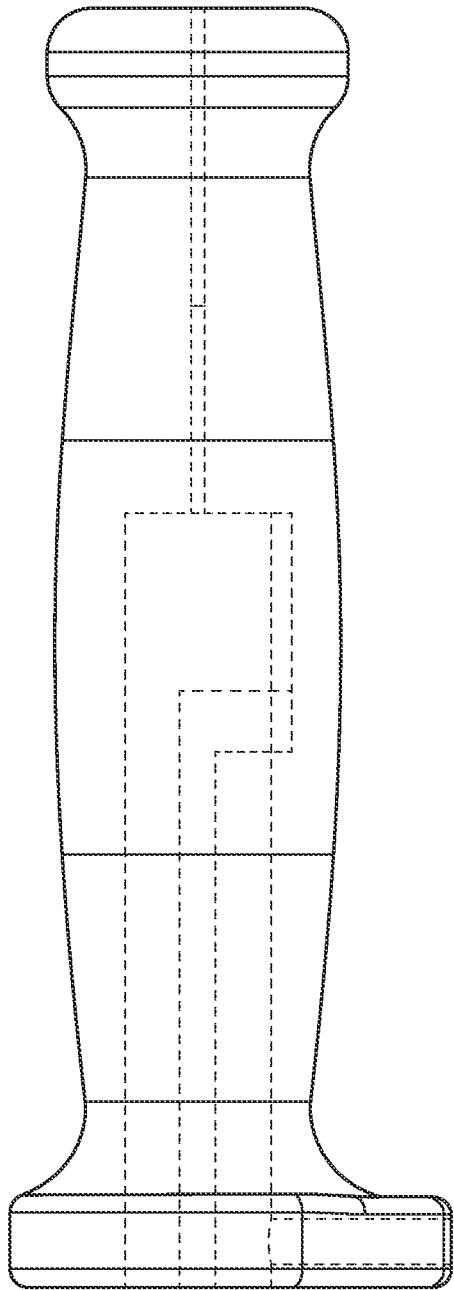
FIG. 20 schematically shows a side view of internal mechanism placement of a deployment system according to an illustrative embodiment.
Figure 21:
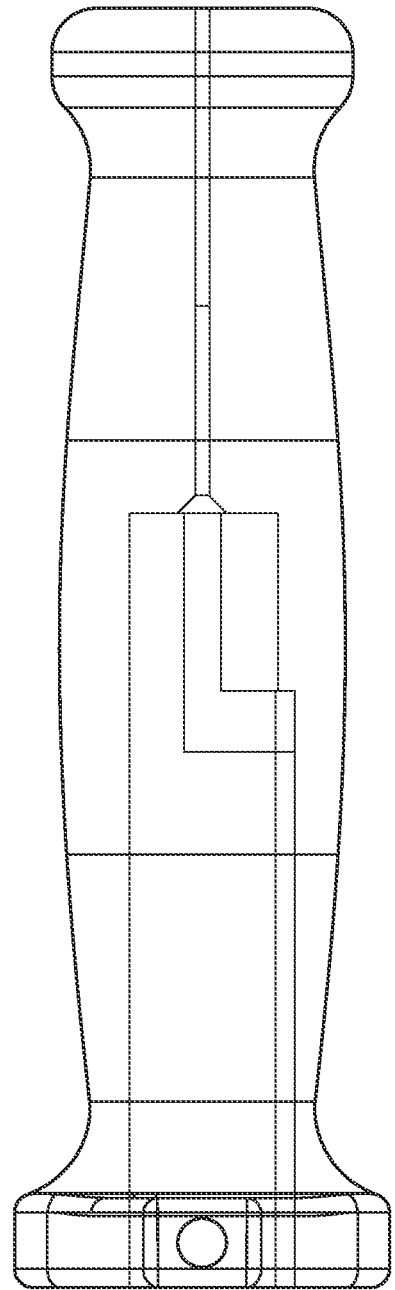
FIG. 21 schematically shows a top view of internal mechanism placement of a deployment system according to an illustrative embodiment.

FIGS. 19 and 20 show a side hidden view assembly of an optional apparatus structure. FIGS. 19 and 20 schematically show the drive hub 70 engaged within the handle 80. The handle 80 includes a channel to guide the needle 50. FIG. 21 shows a top hidden view assembly of the optional apparatus structure, including the drive hub 70 engaged within the handle 80, and the channel to guide the needle 50.

Figure 22:
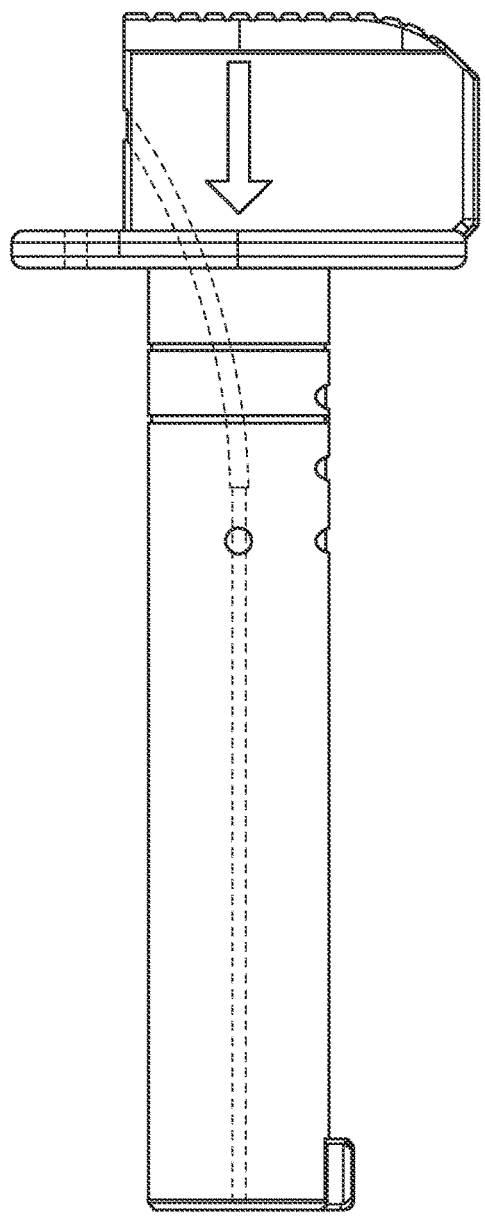
FIG. 22 schematically shows a side view of the drive hub and suture path according to an illustrative embodiment.
Figure 23:
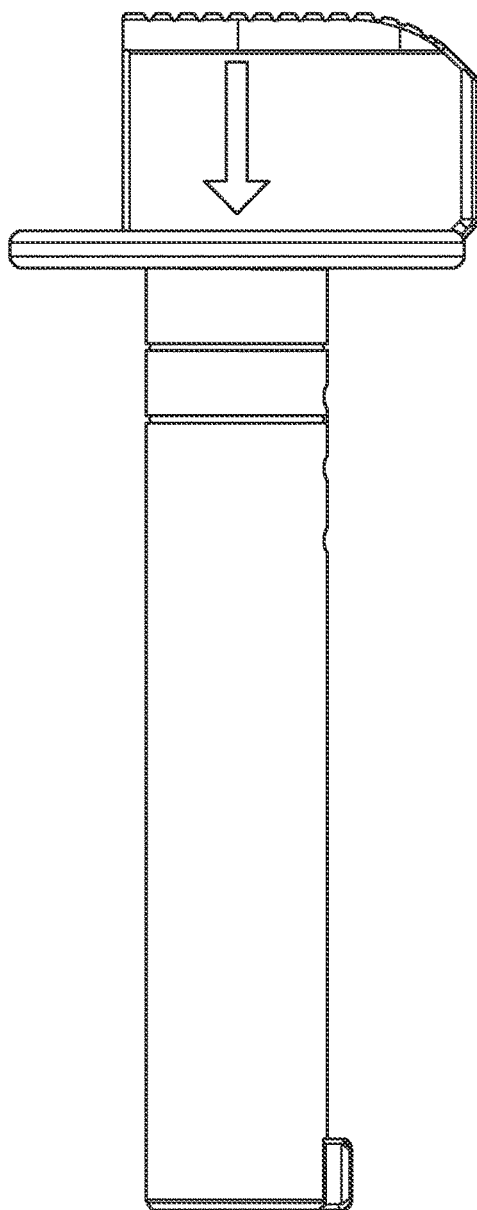
FIG. 23 schematically shows a side view of the drive hub according to an illustrative embodiment.
Figure 24:
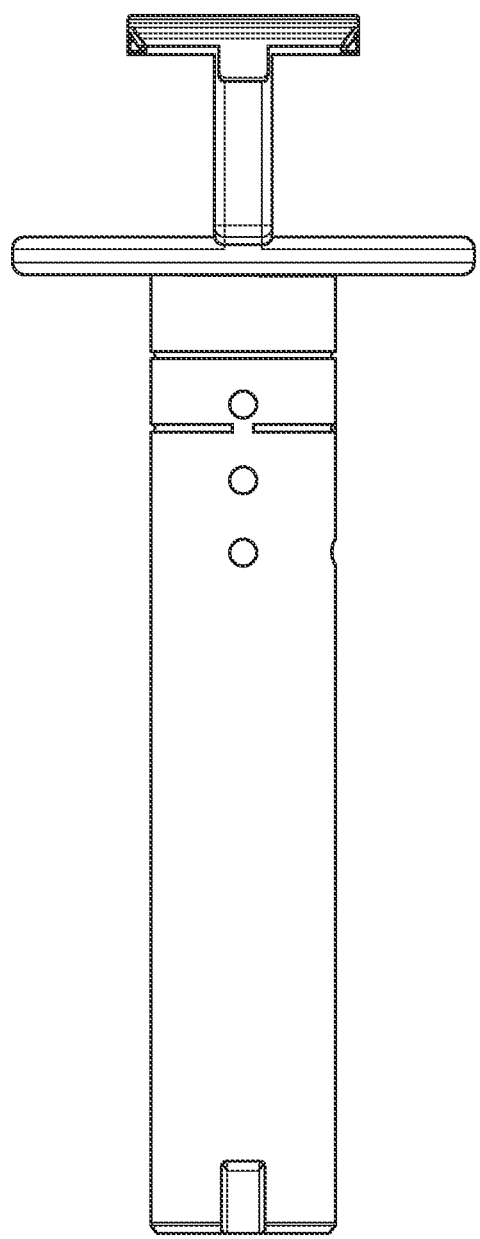
FIG. 24 schematically shows a top view of the drive hub according to an illustrative embodiment.

FIG. 22 schematically shows a side hidden view of the drive hub 70. FIG. 22 details the channel for the suture 40, detents, indicators 73, and ball plunger 72. The arrow indicates the direction that the ball plunger 72 is depressed to deploy the suture 40. FIG. 23 shows a side view of the drive hub 70, and FIG. 24 schematically shows a top view of the drive hub 70.

Figure 25:
FIG. 25 schematically shows a side view of an anchor strip according to an illustrative embodiment.
Figure 26:
FIG. 26 schematically shows a side view of an anchor strip according to an illustrative embodiment.
Figure 27:
FIG. 27 schematically shows a side view of an anchor strip according to an illustrative embodiment.

FIG. 25 schematically shows a side view of anchor strip 1 which includes three anchors 2, 3, 4 and a holder 5 all connected by notches 8. Anchor 2 is the initial primary anchor 2 followed by secondary anchors 3 and 4. FIG. 26 schematically shows a top view of anchor strip 1 with suture holes 6 and suture knot groove 7 with suture hole 16 which is where the knot placement is located on top of. It also depicts suture grooves 9. Knot groove 7 is larger than suture slots 9 to allow for the increased size associated with a knot. FIG. 27 schematically shows a side silhouette view of the anchor strip 1.

Figure 28:
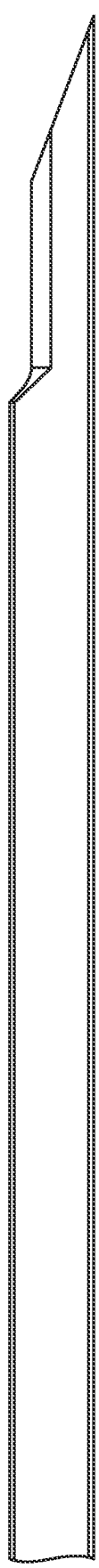
FIG. 28 schematically shows a side view of a needle according to an illustrative embodiment.

FIG. 28 schematically shows the needle 50 having an optional angular taper design. The needle 50 is pushed into ultrasound view as with a standard fine needle aspiration (FNA). The needle 50 is carefully pushed under ultrasound guidance through the wall of the tissue and once we are ensured on ultrasound that the needle 50 is full thickness the anchor 1 is deployed as per FIG. 14. When there is little space for deployment, the needle is pushed past the wall to ensure a transmural (trans/serosal) penetration, pulled back just to the edge of the tissue wall and deployed as the user simultaneously pulls the needle back.

In an alternate embodiment, when there is little or no separation between luminal peritoneal structures, such as for example, the gallbladder or liver abutting the stomach, one may inject a solution/gel through the needle 50 to create a space before inserting the T tag. This technique may involve inserting the needle to adequately ensure the serosa is transversed and then pulling the needle back to an edge of the tissue. At that point, the anchor is pushed out as the needle is pulled back, which allows for an "in place" deployment when there is limited separation or space between luminal peritoneal structures.

Figure 29:
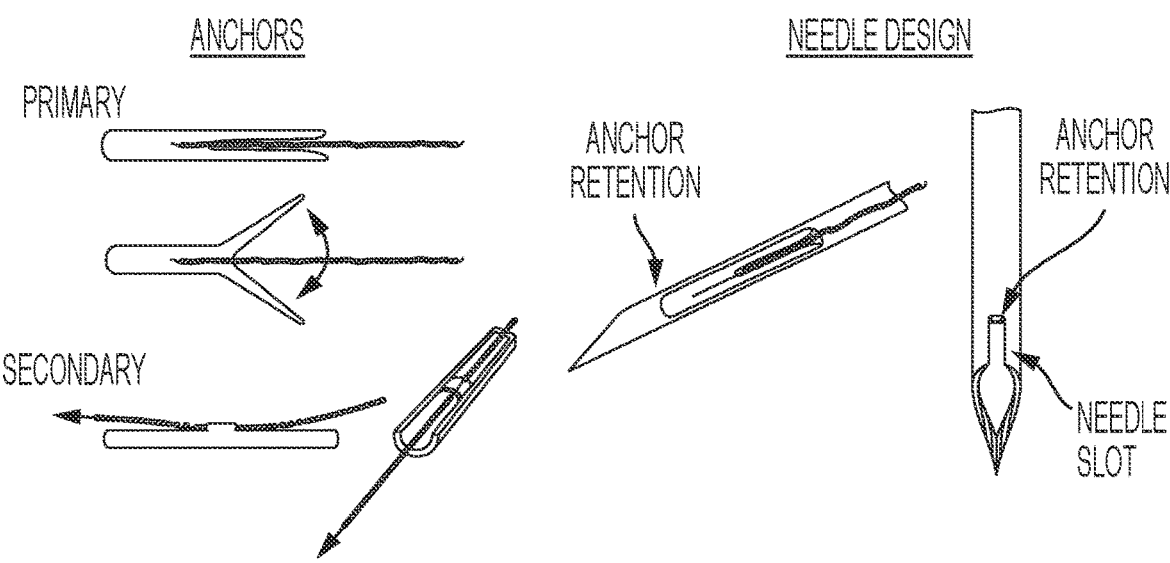
FIG. 29 schematically shows a plurality of optional anchors and corresponding needles according to illustrative embodiments.
Figure 30:
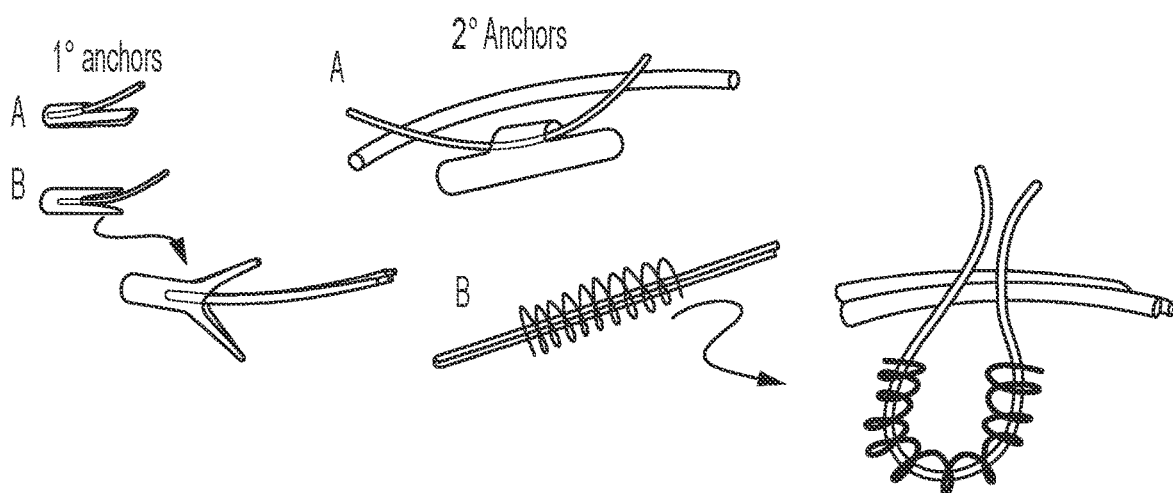
FIG. 30 schematically shows a plurality of optional anchors according to illustrative embodiments.

FIGS. 29 and 30 schematically show optional anchor and needle tip configurations. As shown in FIGS. 29 and 30, the needle tip can be tailored to correspond to the desired anchor configuration. Optional anchor configurations can include expanding anchors, looped anchors, through-body anchors, helical anchors, Y-shaped anchors, or the like.

Anchor material can be varied according to application. Primary and secondary anchors also need not be of the same material. Transmural anchors will need to be made of a material that is accepted by the human body (i.e. stainless steel, nitinol, etc.). It can also be made of a bio-absorbable material. In most applications sutures are not meant to keep tissue apposed for many months. Instead scar formation and body healing take over making the suture less important as time goes on. Polygycolic acid (PGA) can be used to form the anchors the suture line. This means that the anchors, even though transmural, would effectively be absorbed many months out so they are not of any concern in the long term.

Figure 31:
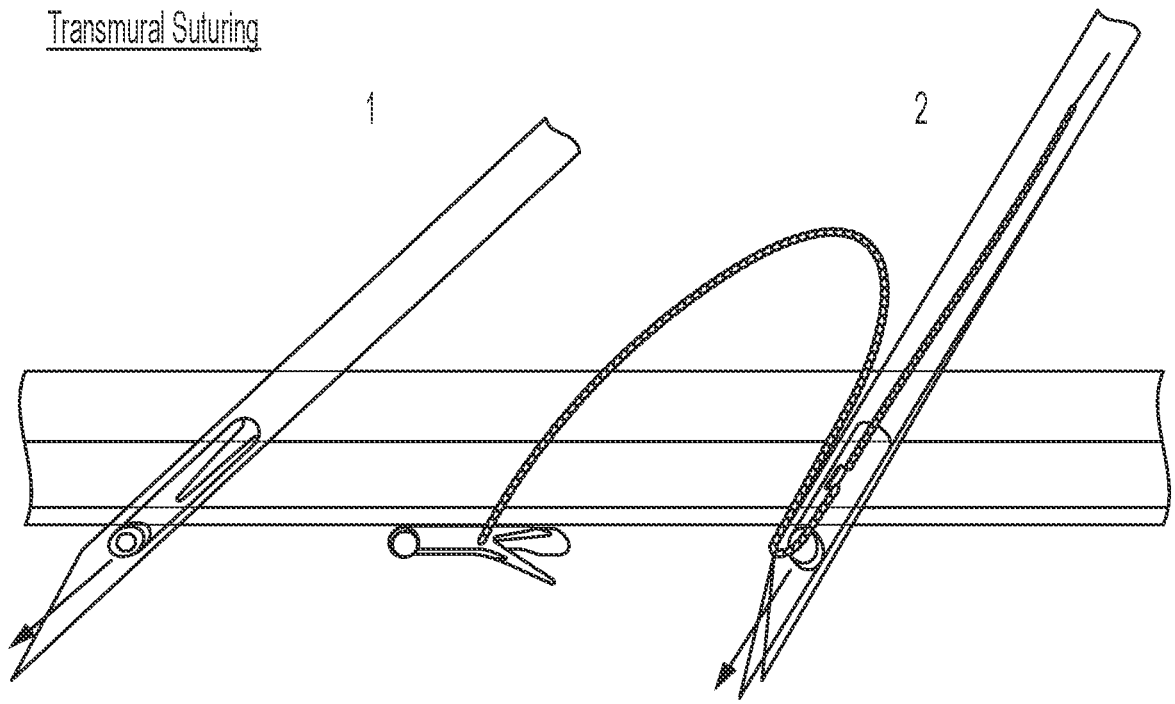
FIG. 31 schematically shows a transmural suturing method according to an illustrative embodiment.
Figure 32:
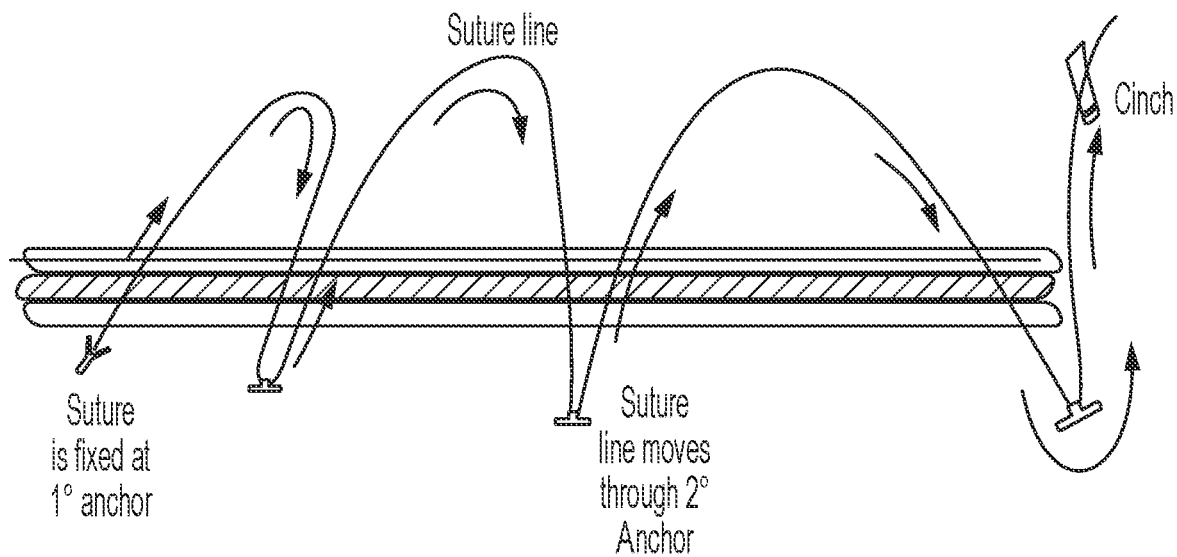
FIG. 32 schematically shows a transmural suturing method according to an illustrative embodiment.

FIGS. 31 and 32 schematically show a suturing procedure as described above. Notably, FIG. 31 illustrates insertion of the needle 50 at step (1) and primary anchor 2 deployment, the trailing suture 40, and a second needle 50 insertion at step (2). FIG. 32 illustrates a complete suturing procedure wherein four anchors 1 are deployed and linked by the suture 40. The suture 40 can be cinched by pulling the suture 40. Cinching the suture 40 closes the opening in the flesh.

Figure 33:
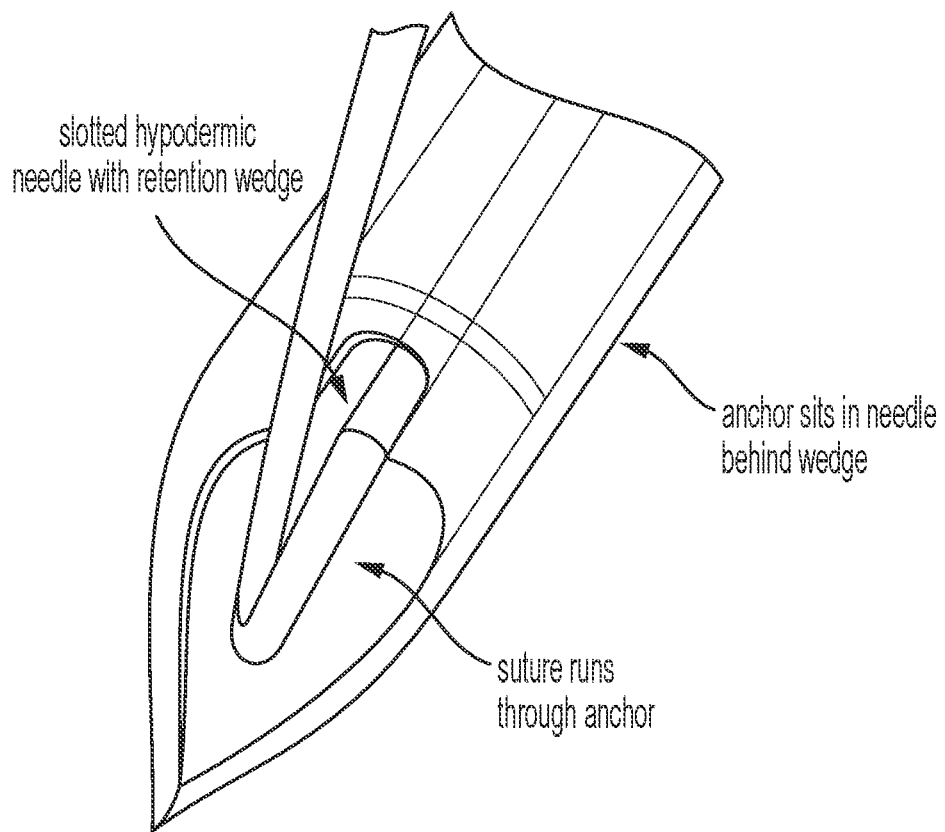
FIG. 33 schematically shows the deployment system prepared for deployment according to an illustrative embodiment.
Figure 34:
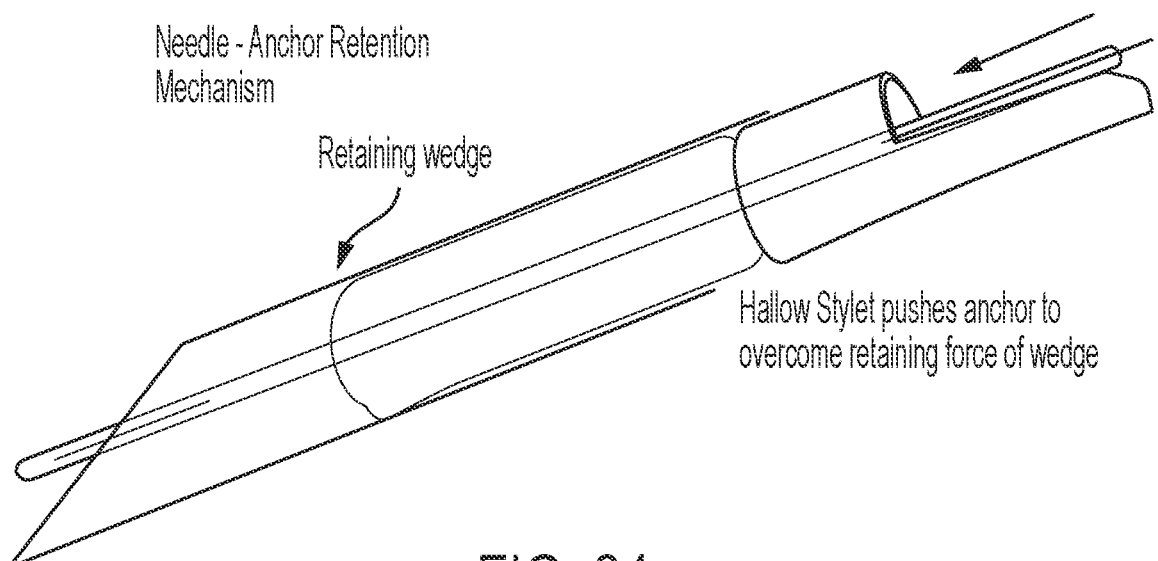
FIG. 34 schematically shows the deployment system deploying the anchor according to an illustrative embodiment.

FIGS. 33 and 34 schematically illustrate the needle anchor retention mechanism that enables the needle 50 to be loaded with the anchor strip 1 and suture 40. The anchor strip 1 is positioned behind the retention wedge and held in place by the wedge. The drive hub (not shown) includes a stylet configured to push the anchor strip past the retention wedge and begin the anchor 1 deployment. Finally, the needle 50 and stylet are hollow to allow passage of the suture 40.

The needle anchor retention mechanism allows for the anchor to sit reliably just before the tip of the needle. Without it, inadvertent premature deployment or accidentally being pushed out with simple maneuvers of the scope. The wedge will yield to pressure from the pushing stylet as the anchor is being delivered. By having such a wedge mechanism, the suture line is able to run down the center of the needle and through each anchor that is being deployed. This is the key to deploying multiple anchors in complex patterns.

Similarly, the pushing stylet allows the suture to run down its center. anchors are loaded and delivered to the distal tip of the needle with the pushing stylet. The suture line runs through the entire needle and anchor. Other variations of the needle can be conceived that allow for multiple secondary anchors to come pre-loaded with the needle. Once again in this situation, the wedge allows for single anchor deployment, while a position is chosen for the next anchor placement.

Summary of features of the present disclosure include: EUS guided system using current EUS platforms and EUS needle-based technology users can adapt readily; Needle based anchor deployment system with a linear mechanism of action eliminates any suture management problems; tissue anchors are deployed through the needle in a EUS guided transmural fashion; anchors can be simple T tags or three prong anchor design (e.g., a trident). Tags or anchors can be made from nitinol or even from absorbable material (e.g., PGA). In addition due to the design of the system, we can provide many options as far as suture material (e.g., absorbable v. non-absorbable, braided v. non-braided, 0 v. 2-0, etc.).

In an alternate embodiment, the present disclosure provides solutions for any T tags or similar anchors being located on a serosal side of an organ and either eroding or migrating into or adjacent other organs, such as, for example, into the mediastinum. Since the T tags or anchors are linearly deployed and are under tension during deployment, such do not create a crossing suture effect. In fact, any erosion or migration will be inward assuming there is tension on the sutures when applied.

Anchors ride independently on the suture line and are then cinched at the end; every fastener acts as a transmural anchor while the cinch rests on the luminal side. An anchor retention wedge allows suture and needle to move freely until anchor is ready to be deployed through tissue-Multiple anchors can thus be deployed in succession over the same suture. This is a major innovation over past prototypes and designs which required two independent sutures and anchors to be cinched together. Past designs did not allow for more than two-point approximation. Our solution is scalable depending on how many anchors are deployed transmurally.

What is claimed is:

1. A suture anchor system, comprising:
a hypodermic needle;
an anchor strip of linear disposition formed from a single continuous section of material, comprising:
a plurality of suture anchors with breakaway sections between adjacent suture anchors;
a suture connected to the plurality of suture anchors;
a drive hub, configured to advance the suture anchors out of the hypodermic needle when pushed;
a handle configured to allow manual operation of the suture anchor system; and
a ball plunger that protrudes from the handle and allows manual operation of the suture anchor system.

2. The suture anchor system of claim 1, wherein the hypodermic needle is a hollow hypodermic needle comprising an endoscopic needle or an endoscopic ultrasound needle.

3. The suture anchor system of claim 2, wherein the plurality of suture anchors is configured to be loaded inside the hollow hypodermic needle.

4. The suture anchor system of claim 1, wherein the drive hub is configured to drive the plurality of suture anchors into a subject's flesh.

5. The suture anchor system of claim 1, wherein the plurality of suture anchors comprises at least a primary suture anchor.

6. The suture anchor system of claim 5, wherein the plurality of suture anchors comprises suture holes and suture knot grooves configured to separate the primary suture anchor from the plurality of suture anchors after insertion into a subject's flesh.

7. The suture anchor system of claim 6, wherein the suture anchor system is configured to insert the plurality of suture anchors into the subject's flesh as needed to suture an opening in the subject's flesh.

8. The suture anchor system of claim 1, wherein the handle is configured to house the drive hub and hypodermic needle.

9. The suture anchor system of claim 1, further comprising:
 a pusher, rigidly connected to the drive hub and a proximal end of the anchor strip, configured to control the anchor strip in response to drive hub movement, wherein the pusher is hollow and is configured to allow the suture to pass therethrough.

10. A method of suturing an opening in a subject's flesh, comprising:
 preparing a suture anchor system by:
  threading a length of a suture through an anchor strip, the anchor strip having a linear disposition and formed from a continuous section of material, the anchor strip comprising a plurality of suture anchors joined by breakaway sections between adjacent suture anchors; and
  loading a hypodermic needle with the anchor strip;
 deploying a primary suture anchor into a primary suture anchor point in a subject's flesh by:
  inserting the hypodermic needle loaded with the anchor strip into the subject's flesh;
  grasping a handle allowing manual operation of the suture anchor system;
  pushing a drive hub to advance the primary suture anchor out of the hypodermic needle, a ball plunger protruding from the handle and engaging the drive hub; and
  retracting the hypodermic needle;
 moving the hypodermic needle to a second suture anchor point;
  deploying a secondary suture anchor in the second suture anchor point by:
   inserting the hypodermic needle into the subject's flesh;
   pushing the drive hub to advance the secondary suture anchor out of the hypodermic needle, the plurality of suture anchors comprising at least the primary and the secondary suture anchors; and
   retracting the hypodermic needle;
 repeating deploying suture anchors of the plurality of suture anchors as needed; and
 cinching the suture.

11. The method of claim 10, wherein deploying the primary suture anchor comprises driving the primary suture anchor into an interior side of the flesh being sutured.

12. The method of claim 11, wherein once driven into the interior side of the flesh, applying tension to the suture to break away the primary suture anchor from the plurality of suture anchors.

13. The method of claim 10, wherein retracting the hypodermic needle comprises feeding the suture from an interior of the flesh to an exterior of the flesh.

14. The method of claim 10, wherein moving the needle to the secondary suture anchor point comprises determining a suture spacing sufficient to optimize healing.

15. The method of claim 10, wherein deploying the secondary suture anchor comprises driving the secondary suture anchor into an interior of the flesh and breaking away the secondary suture anchor from the plurality of suture anchors.

16. The method of claim 10, wherein cinching the suture comprises pulling the suture such that the plurality of suture anchors and the suture urge the flesh together in order to induce healing.

17. The method of claim 10, further comprising:
 translating drive hub movement into anchor strip movement by a pusher, rigidly connected to the drive hub and a proximal end of the anchor strip, wherein the pusher is hollow, allowing the suture to pass therethrough.

* * * * *